US011046673B1

(12) United States Patent
Akioka et al.

(10) Patent No.: US 11,046,673 B1
(45) Date of Patent: Jun. 29, 2021

(54) TETRAZOLINONE COMPOUNDS AND ITS USE

(71) Applicant: SUMITOMO CHEMICAL COMPANY, LIMITED, Tokyo (JP)

(72) Inventors: Yuki Akioka, Takarazuka (JP); Nao Maehata, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 337 days.

(21) Appl. No.: 16/326,003

(22) PCT Filed: Aug. 24, 2017

(86) PCT No.: PCT/JP2017/030279
§ 371 (c)(1),
(2) Date: Feb. 15, 2019

(87) PCT Pub. No.: WO2018/038200
PCT Pub. Date: Mar. 1, 2018

(30) Foreign Application Priority Data

Aug. 25, 2016 (JP) .............................. JP2016-164472

(51) Int. Cl.
C07D 403/12 (2006.01)
A01N 43/713 (2006.01)

(52) U.S. Cl.
CPC ......... *C07D 403/12* (2013.01); *A01N 43/713* (2013.01)

(58) Field of Classification Search
CPC .......................... C07D 403/12; A01N 43/713
USPC ....................................................... 514/381
See application file for complete search history.

(56) References Cited

U.S. PATENT DOCUMENTS

2017/0105413 A1    4/2017  Akioka et al.

FOREIGN PATENT DOCUMENTS

| CN | 104684908 A | 6/2015 |
| EP | 3 006 440 B1 | 3/2018 |
| JP | 2015-27978 A | 2/2015 |
| WO | WO 2014/051161 A1 | 4/2014 |
| WO | WO 2014/051165 A1 | 4/2014 |
| WO | WO 2015/050039 A1 | 4/2015 |
| WO | WO 2015/050040 A1 | 4/2015 |
| WO | WO 2015/147314 A1 | 10/2015 |

OTHER PUBLICATIONS

Indian Office Action for Indian Application No. 201947006792, dated Nov. 23, 2020, with English translation.
International Preliminary Report on Patentability and Written Opinion of the International Searching Authority issued in the corresponding International Application No. PCT/JP2017/030279 dated Feb. 26, 2019.
International Search Report issued in the corresponding International Application No. PCT/JP2017/030279 dated Dec. 5, 2017.
Chinese Office Action and Search Report, dated Aug. 20, 2020, for Chinese Application No. 201780051068.4, with English translation of the Chinese Office Action.
Japanese Office Action and Japanese Application No. 2019-507962, dated Apr. 13, 2021, with English translation.

Primary Examiner — Kristin A Vajda
(74) Attorney, Agent, or Firm — Birch, Stewart, Kolasch & Birch, LLP

(57) ABSTRACT

The present invention provides a compound having excellent control efficacies against plant diseases. The compound is represented by formula (I): wherein, $R^1$ represents a C1-C3 alkyl group optionally having one or more halogens; n is 1 or 2; $R^2$ and $R^3$ represent independently of each other a hydrogen atom, etc.; $R^4$ represents a hydrogen atom, etc.; and $R^5$ represents a C1-C3 alkyl group optionally having one or more halogen atoms, etc.

5 Claims, No Drawings

TETRAZOLINONE COMPOUNDS AND ITS USE

TECHNICAL FIELD

This application claims priority to and the benefit of Japanese Patent Application No. 2016-164472 filed Aug. 25, 2016, the entire contents of which are incorporated herein by reference.

The present invention relates to tetrazolinone compounds, an agent for controlling plant diseases which comprises the same, and their use.

BACKGROUND ART

Heretofore, various compounds have been developed to control plant diseases (see Patent Document 1).

CITATION LIST

Patent Literature

PTL 1: WO 2014/051165 pamphlet

SUMMARY OF INVENTION

Technical Problem

An object of the present invention is to provide a compound having an excellent efficacy for controlling pests.

Solution to Problem

The present inventors have intensively studied to find that compounds having an excellent efficacy for controlling pests and as a result, found that a compound represented by the below-mentioned formula (I) has an excellent efficacy for controlling plant diseases, which thus have completed the present invention.

That is, the present invention includes the followings.
[1] A compound represented by a formula (I):

[Chem.1]

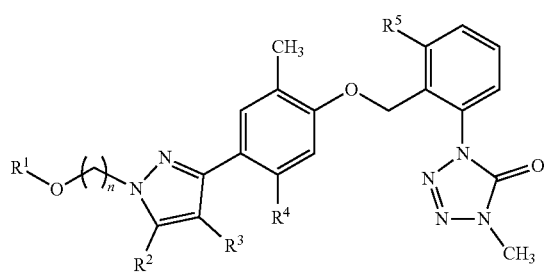

(I)

wherein,
$R^1$ represents a C1-C3 alkyl group optionally having one or more halogens;
n is 1 or 2;
$R^2$ and $R^3$ each independently represent a hydrogen atom, a halogen atom, or a C1-C3 alkyl group;
$R^4$ represents a hydrogen atom or a methyl group; and
$R^5$ represents a C1-C3 alkyl group optionally having one or more halogen atoms, a C1-C3 alkoxy group optionally having one or more halogen atoms, a hydrogen atom, a halogen atom, or a C3-C4 cycloalkyl group optionally having one or more halogen atoms. (hereinafter, referred to as "Present compound" or "Compound of the present invention").

[2] The compound described in [1] wherein
$R^1$ represents a C1-C3 alkyl group,
$R^2$ and $R^3$ each independently represent a hydrogen atom, a halogen atom, or a methyl group; and
$R^5$ represents a hydrogen atom, a halogen atom, a C1-C3 alkyl group, a C1-C3 alkoxy group or a cyclopropyl group.
[3] The compound described in [1] or [2] wherein
$R^2$ represents a hydrogen atom or a methyl group,
$R^3$ represents a hydrogen atom; and
$R^5$ represents a C1-C3 alkyl group.
[4] An agent for controlling plant a disease which comprises the compound described in [1] to [3] (hereinafter, referred to as "Present control agent" or "Control agent of the present invention").
[5] A method for controlling plant diseases which comprises applying an effective amount of the compound described in [1] to [3] to plant or soil.
[6] Use of the compound described in [1] to [3] for controlling a plant disease.

The present invention can control plant diseases.

DESCRIPTION OF EMBODIMENTS

The substituent(s) as described herein is/are explained.

Herein when two or more halogen atoms are present, these halogen atoms may be identical to or different from each other.

The expression f "CX-CY" to be used herein represents that the number of carbon atom is from X to Y. For example, the expression of "C1-C3" represents that the number of carbon atom is 1 to 3.

The term "halogen atom" to be used herein represents, for example, a fluorine atom, a chlorine atom, a bromine atom or an iodine atom, The term of "C1-C3 alkyl group" to be used herein represents, for example, a methyl group, an ethyl group, a propyl group, or an isopropyl group.

The term of "C1-C3 alkoxy group" to be used herein represents, for example, a methoxy group, an ethoxy group, a propoxy group, or an isopropoxy group. The term of "C3-C4 cycloalkyl group" to be used herein represents, for example, a cy-cloproply group or a cyclobutyl group.

Examples of the present compound include the following compounds.

[Embodiment 1] a compound of the present invention wherein $R^2$ and $R^3$ represent independently of each other a hydrogen atom, a bromine atom, a chlorine atom, a fluorine atom, or a methyl group;

[Embodiment 2] a compound described in [Embodiment 1] wherein $R^4$ represents a hydrogen atom;

[Embodiment 3] a compound described in [Embodiment 1] wherein $R^4$ represents a methyl group;

[Embodiment 4] a compound described in [Embodiment 1] wherein $R^5$ represents a hydrogen atom, or a C1-C3 alkyl group optionally having one or more halogen atoms;

[Embodiment 5] a compound described in [Embodiment 1] wherein $R^5$ represents a C1-C3 alkyl group optionally having one or more halogen atoms;

[Embodiment 6] a compound described in [Embodiment 1] wherein $R^5$ represents a hydrogen atom or a C1-C3 alkyl group;

[Embodiment 7] a compound described in [Embodiment 1] wherein $R^5$ represents a C1-C3 alkyl group;

[Embodiment 8] a compound described in [Embodiment 1] wherein $R^5$ represents a hydrogen atom, a halogen atom, a methyl group, an ethyl group, a methoxy group, or a cyclopropyl group;

[Embodiment 9] a compound described in [Embodiment 1] wherein $R^5$ represents a hydrogen atom, a chorine atom, a fluorine atom, a methyl group, an ethyl group, a methoxy group, or a cyclopropyl group;

[Embodiment 10] a compound described in [Embodiment 1] wherein $R^5$ represents a hydrogen atom or a methyl group;

[Embodiment 11] a compound described in [Embodiment 1] wherein $R^5$ represents a methyl group;

[Embodiment 12] a compound of the present invention wherein $R^2$ and $R^3$ represent independently of each other a hydrogen atom, or a methyl group;

[Embodiment 13] a compound described in [Embodiment 12] wherein $R^4$ represents a hydrogen atom;

[Embodiment 14] a compound described in [Embodiment 12] wherein $R^4$ represents a methyl group;

[Embodiment 15] a compound described in [Embodiment 12] wherein $R^5$ represents a hydrogen atom, or a C1-C3 alkyl group optionally having one or more halogen atoms;

[Embodiment 16] a compound described in [Embodiment 12] wherein $R^5$ represents a C1-C3 alkyl group optionally having one or more halogen atoms;

[Embodiment 17] a compound described in [Embodiment 12] wherein $R^5$ represents a hydrogen atom, or a C1-C3 alkyl group;

[Embodiment 18] a compound described in [Embodiment 12] wherein $R^5$ represents a C1-C3 alkyl group;

[Embodiment 19] a compound described in [Embodiment 12] wherein $R^5$ represents a hydrogen atom, a halogen atom, a methyl group, an ethyl group, a methoxy group, or a cyclopropyl group;

[Embodiment 20] a compound described in [Embodiment 12] wherein $R^5$ represents a hydrogen atom, a chlorine atom, a fluorine atom, a methyl group, an ethyl group, a methoxy group, or a cyclopropyl group;

[Embodiment 21] a compound described in [Embodiment 12] wherein $R^5$ represents a hydrogen atom or a methyl group;

[Embodiment 22] a compound described in [Embodiment 12] wherein $R^5$ represents a methyl group;

[Embodiment 23] a compound of the present invention wherein $R^2$ and $R^3$ represent independently of each other a hydrogen atom;

[Embodiment 24] a compound described in [Embodiment 23] wherein $R^4$ represents a hydrogen atom;

[Embodiment 25] a compound described in [Embodiment 23] wherein $R^4$ represents a methyl group;

[Embodiment 26] a compound described in [Embodiment 23] wherein $R^5$ represents a hydrogen atom, or a C1-C3 alkyl group optionally having one or more halogen atoms;

[Embodiment 27] a compound described in [Embodiment 23] wherein $R^5$ represents a C1-C3 alkyl group optionally having one or more halogen atoms;

[Embodiment 28] a compound described in [Embodiment 23] wherein $R^5$ represents a hydrogen atom, or a C1-C3 alkyl group;

[Embodiment 29] a compound described in [Embodiment 23] wherein $R^5$ represents a C1-C3 alkyl group;

[Embodiment 30] a compound described in [Embodiment 23] wherein $R^5$ represents a hydrogen atom, a halogen atom, a methyl group, an ethyl group, a methoxy group, a cyclopropyl group;

[Embodiment 31] a compound described in [Embodiment 23] wherein $R^5$ represents a hydrogen atom, a chlorine atom, a fluorine atom, a methyl group, an ethyl group, a methoxy group, or a cyclopropyl group;

[Embodiment 32] a compound described in [Embodiment 23] wherein $R^5$ represents a hydrogen atom or a methyl group;

[Embodiment 33] a compound described in [Embodiment 23] wherein $R^5$ represents a methyl group;

[Embodiment 34] a compound described in [Embodiment 4] wherein $R^4$ represents a hydrogen atom;

[Embodiment 35] a compound described in [Embodiment 5] wherein $R^4$ represents a hydrogen atom;

[Embodiment 36] a compound described in [Embodiment 6] wherein $R^4$ represents a hydrogen atom;

[Embodiment 37] a compound described in [Embodiment 7] wherein $R^4$ represents a hydrogen atom;

[Embodiment 38] a compound described in [Embodiment 8] wherein $R^4$ represents a hydrogen atom;

[Embodiment 39] a compound described in [Embodiment 9] wherein $R^4$ represents a hydrogen atom;

[Embodiment 40] a compound described in [Embodiment 10] wherein $R^4$ represents a hydrogen atom;

[Embodiment 41] a compound described in [Embodiment 11] wherein $R^4$ represents a hydrogen atom;

[Embodiment 42] a compound described in [Embodiment 15] wherein $R^4$ represents a hydrogen atom;

[Embodiment 43] a compound described in [Embodiment 16] wherein $R^4$ represents a hydrogen atom;

[Embodiment 44] a compound described in [Embodiment 17] wherein $R^4$ represents a hydrogen atom;

[Embodiment 45] a compound described in [Embodiment 18] wherein $R^4$ represents a hydrogen atom;

[Embodiment 46] a compound described in [Embodiment 19] wherein $R^4$ represents a hydrogen atom;

[Embodiment 47] a compound described in [Embodiment 20] wherein $R^4$ represents a hydrogen atom;

[Embodiment 48] a compound described in [Embodiment 21] wherein $R^4$ represents a hydrogen atom;

[Embodiment 49] a compound described in [Embodiment 22] wherein $R^4$ represents a hydrogen atom;

[Embodiment 50] a compound described in [Embodiment 26] wherein $R^4$ represents a hydrogen atom;

[Embodiment 51] a compound described in [Embodiment 27] wherein $R^4$ represents a hydrogen atom;

[Embodiment 52] a compound described in [Embodiment 28] wherein $R^4$ represents a hydrogen atom;

[Embodiment 53] a compound described in [Embodiment 29] wherein $R^4$ represents a hydrogen atom;

[Embodiment 54] a compound described in [Embodiment 30] wherein $R^4$ represents a hydrogen atom;

[Embodiment 55] a compound described in [Embodiment 31] wherein $R^4$ represents a hydrogen atom;

[Embodiment 56] a compound described in [Embodiment 32] wherein $R^4$ represents a hydrogen atom;

[Embodiment 57] a compound described in [Embodiment 33] wherein $R^4$ represents a hydrogen atom;

[Embodiment 58] a compound described in any one of [Embodiments 1 to 57] wherein $R^1$ represents a methyl group or an ethyl group;

[Embodiment 59] a compound described in any one of [Embodiments 1 to 57] wherein $R^1$ represents a methyl group;

[Embodiment 60] a compound described in any one of [Embodiments 1 to 57] wherein $R^1$ represents an ethyl group;

[Embodiment 61] a compound described in any one of [Embodiments 1 to 57] wherein $R^1$ represents a methyl group or an ethyl group, and n is 1;

[Embodiment 62] a compound described in any one of [Embodiments 1 to 57] wherein $R^1$ represents a methyl group, and n is 1;

[Embodiment 63] a compound described in any one of [Embodiments 1 to 57] wherein $R^1$ represents an ethyl group, and n is 1;

[Embodiment 64] a compound described in any one of [Embodiments 1 to 57] wherein $R^1$ represents a methyl group or an ethyl group, and n is 2;

[Embodiment 65] a compound described in any one of [Embodiments 1 to 57] wherein $R^1$ represents a methyl group, and n is 2;

[Embodiment 66] a compound described in any one of [Embodiments 1 to 57] wherein $R^1$ represents an ethyl group, and n is 2;

[Embodiment 67] a compound of the present invention wherein $R^1$ represents a methyl group or an ethyl group;

[Embodiment 68] a compound of the present invention wherein $R^1$ represents a methyl group;

[Embodiment 69] a compound of the present invention wherein $R^1$ represents an ethyl group;

[Embodiment 70] a compound of the present invention wherein $R^1$ represents a methyl group or an ethyl group, and n is 1;

[Embodiment 71] a compound of the present invention wherein $R^1$ represents a methyl group, and n is 1;

[Embodiment 72] a compound of the present invention wherein $R^1$ represents an ethyl group, and n is 1;

[Embodiment 73] a compound of the present invention wherein $R^1$ represents a methyl group or an ethyl group, and n is 2;

[Embodiment 74] a compound of the present invention wherein $R^1$ represents a methyl group, and n is 2;

[Embodiment 75] a compound of the present invention wherein $R^1$ represents an ethyl group, and n is 2;

[Embodiment 76] a compound of the present invention wherein $R^1$ represents a methyl group or an ethyl group, and $R^5$ represents a C1-C3 alkyl group optionally having one or more halogen atoms, or a hydrogen atom;

[Embodiment 77] a compound of the present invention wherein $R^1$ represents a methyl group or an ethyl group, and $R^5$ represents a C1-C3 alkyl group or a hydrogen atom;

[Embodiment 78] a compound of the present invention wherein $R^1$ represents a methyl group or an ethyl group, and $R^2$ and $R^3$ represent independently of each other a hydrogen atom, a halogen atom, or a methyl group, and $R^5$ represents a C1-C3 alkyl group or a hydrogen atom;

[Embodiment 79] a compound of the present invention wherein $R^1$ represents a methyl group or an ethyl group, $R^2$ and $R^3$ represent independently of each other a hydrogen atom, a halogen atom, or a methyl group, and $R^5$ represents a hydrogen atom or a methyl group;

[Embodiment 80] a compound of the present invention wherein $R^1$ represents a methyl group, n is 1, and $R^5$ represents a C1-C3 alkyl group optionally having one or more halogen atoms, or a hydrogen atom;

[Embodiment 81] a compound of the present invention wherein $R^1$ represents a methyl group, n is 1, and $R^5$ represents a C1-C3 alkyl group or a hydrogen atom;

[Embodiment 82] a compound of the present invention wherein $R^1$ represents a methyl group, n is 1, $R^2$ and $R^3$ represent independently of each other a hydrogen atom, a halogen atom, or a methyl group, and $R^5$ represents a C1-C3 alkyl group or a hydrogen atom;

[Embodiment 83] a compound of the present invention wherein $R^1$ represents a methyl group, n is 1, $R^2$ and $R^3$ represent independently of each other a hydrogen atom, a halogen atom, or a methyl group, and $R^5$ represents a hydrogen atom or a methyl group;

[Embodiment 84] a compound of the present invention wherein $R^1$ represents an ethyl group, n is 1, and $R^5$ represents a C1-C3 alkyl group optionally having one or more halogen atoms, or a hydrogen atom;

[Embodiment 85] a compound of the present invention wherein $R^1$ represents an ethyl group, n is 1, and $R^5$ represents a C1-C3 alkyl group or a hydrogen atom;

[Embodiment 86] a compound of the present invention wherein $R^1$ represents an ethyl group, n is 1, $R^2$ and $R^3$ represent independently of each other a hydrogen atom, a halogen atom, or a methyl group, and $R^5$ represent a C1-C3 alkyl group or a hydrogen atom;

[Embodiment 87] a compound of the present invention wherein $R^1$ represents an ethyl group, n is 1, $R^2$ and $R^3$ represent independently of each other a hydrogen atom, a halogen atom, or a methyl group, and $R^5$ represents a hydrogen atom or a methyl group;

[Embodiment 88] a compound of the present invention wherein $R^1$ represents a methyl group, n is 2, and $R^5$ represents a C1-C3 alkyl group optionally having one or more halogen atoms, or a hydrogen atom;

[Embodiment 89] a compound of the present invention wherein $R^1$ represents a methyl group, n is 2, and $R^5$ represents a C1-C3 alkyl group or a hydrogen atom;

[Embodiment 90] a compound of the present invention wherein $R^1$ represents a methyl group, n is 2, and $R^5$ represents a C1-C3 alkyl group;

[Embodiment 91] a compound of the present invention wherein $R^1$ represents a methyl group, n is 2, and $R^5$ represents a methyl group;

[Embodiment 92] a compound of the present invention wherein $R^1$ represents a methyl group, n is 2, $R^2$ and $R^3$ represent independently of each other a hydrogen atom, a halogen atom, or a methyl group, and $R^5$ represent a C1-C3 alkyl group or a hydrogen atom;

[Embodiment 93] a compound of the present invention wherein $R^1$ represents a methyl group, n is 2, $R^2$ and $R^3$ represent independently of each other a hydrogen atom, a halogen atom, a methyl group, and $R^5$ represents a hydrogen atom, or a methyl group;

[Embodiment 94] a compound of the present invention wherein $R^1$ represents a methyl group, n is 2, $R^2$ and $R^3$ represent independently of each other a hydrogen atom, a halogen atom, or a methyl group, and $R^5$ represents a C1-C3 alkyl group;

[Embodiment 95] a compound of the present invention wherein $R^1$ represents a methyl group, n is 2, $R^2$ and $R^3$ represent independently of each other a hydrogen atom, a halogen atom, or a methyl group, and $R^5$ represents a methyl group;

[Embodiment 96] a compound of the present invention wherein $R^1$ represents an ethyl group, n is 2, and $R^5$ represents a C1-C3 alkyl group optionally having one or more halogen atoms, or a hydrogen atom;

[Embodiment 97] a compound of the present invention wherein $R^1$ represents an ethyl group, n is 2, and $R^5$ represents a C1-C3 alkyl group or a hydrogen atom;

[Embodiment 98] a compound of the present invention wherein $R^1$ represents an ethyl group, n is 2, and $R^5$ represents a C1-C3 alkyl group;

[Embodiment 99] a compound of the present invention wherein $R^1$ represents an ethyl group, n is 2, and $R^5$ represents a methyl group;

[Embodiment 100] a compound of the present invention wherein $R^1$ represents an ethyl group, n is 2, $R^2$ and $R^3$ represent independently of each other a hydrogen atom or a methyl group, and $R^5$ represents a C1-C3 alkyl group or a hydrogen atom;

[Embodiment 101] a compound of the present invention wherein $R^1$ represents an ethyl group, n is 2, $R^2$ and $R^3$ represent independently of each other a hydrogen atom or a methyl group, and $R^5$ represents a C1-C3 alkyl group;

[Embodiment 102] a compound of the present invention wherein $R^1$ represents an ethyl group, n is 2, $R^2$ and $R^3$ represent independently of each other a hydrogen atom or a methyl group, and $R^5$ represents a methyl group;

Next, a process for preparing the compound A is explained.

The compound A may be prepared, for example, according to the following processes.

Process A

The compound of the present invention may be prepared by reacting a compound represented by formula (A1) (hereinafter, referred to as Compound (A1)) with a compound represented by formula (A2) (hereinafter, referred to as Compound (A2)) in the presence of a base.

[Chem. 2]

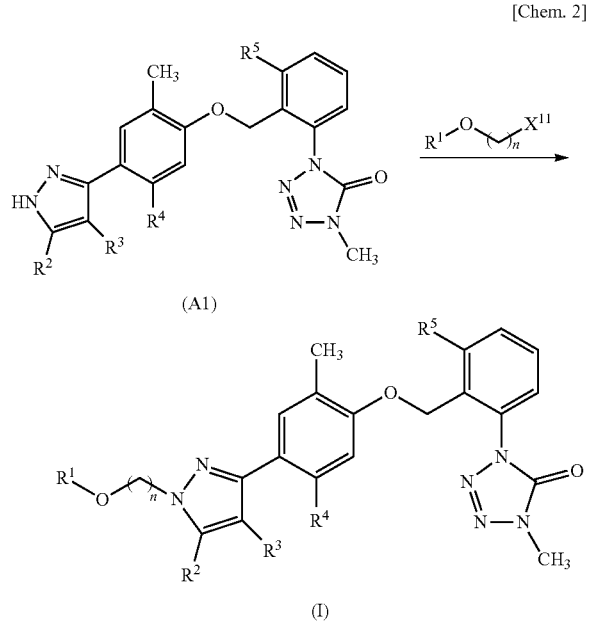

wherein, $X^{11}$ represents a chlorine atom, a bromine atom, an iodine atom, a methane-sulfonyloxy group, or a p-toluenesulfonyloxy group, and the other symbols are the same as defined above.

The reaction is usually carried out in a solvent.

Examples of the solvent to be used in the reaction include hydrocarbons such as n-hexane, cyclohexane, toluene, and xylene; ethers such as tetrahydrofuran (hereinafter, referred to as THF), ethyleneglycol dimethyl ether, and methyl tert-butyl ether (hereinafter, referred to as MTBE); halogenated aliphatic hydrocarbons such as chloroform and dichloromethane; acid amides such as N,N-dimethylformamide (hereinafter, referred to as DMF) and N-methylpyrrolidone; esters such as ethyl acetate; nitriles such as acetonitrile and propionitrile (hereinafter, collectively referred to as nitriles); and mixed solvents thereof.

The base to be used in the reaction include organic bases such as triethylamine and pyridine; alkali metal carbonates such as sodium carbonate, potassium carbonate and cesium carbonate; alkali metal hydrogen carbonates such as sodium hydrogen carbonate and potassium hydrogen carbonate; alkali metal hydroxides such as lithium hydroxide, sodium hydroxide and potassium hydroxide; alkali metal hydrides such as sodium hydride; and alkali metal alkoxides such as sodium tert-butoxide and potassium tert-butoxide.

In the reaction, the compound (A2) is used usually within a range of 1 to 10 molar ratio(s), and the base is used usually within a range of 1 to 10 molar ratio(s), as opposed to 1 mole of the compound (A1).

The reaction temperature is usually within a range of −20 to 150° C. The reaction period of the reaction is usually within a range of 0.1 to 120 hours.

When the reaction is completed, water is added to reaction mixtures, and the reaction mixtures are extracted with organic solvents, and the organic layers are worked up (for example, drying and concentration) to give the compound of the present invention. The compound (A2) may be a known compound, or can be prepared according to the similar method to a known method Reference Process A The compound (A1) may be prepared by reacting a compound represented by formula (B1) (hereinafter, referred to as Compound (B1)) with a compound represented by formula (B2) (hereinafter, referred to as Compound (B2)) in the presence of a base.

[Chem. 3]

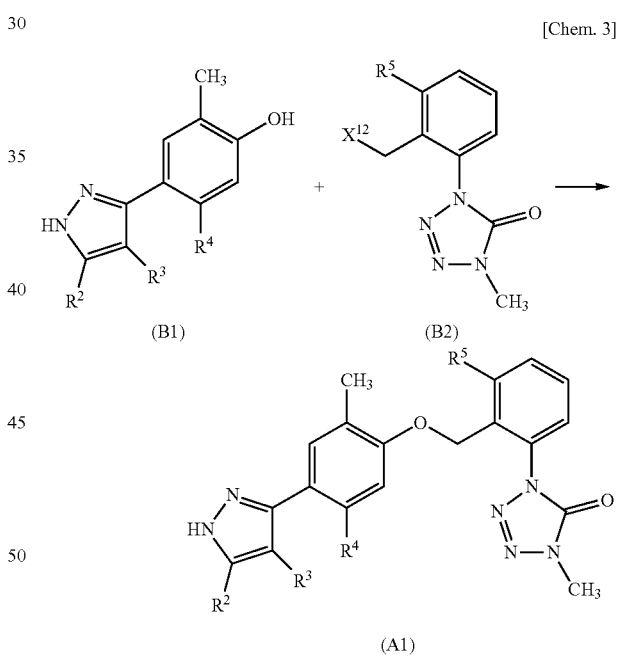

wherein $X^{12}$ represents a chlorine atom, a bromine atom, or an iodine atom, and the other symbols are the same as defined above.

The reaction may be conducted according to a similar method to the process A which is described in WO2014/051165. Also the compound (A1) may be prepared according to a similar method to the process F or the process G each which is described in WO2014/051165.

The compound (B2) may be prepared by the method of the reference process H, the reference process K, or the reference process L each which is described in WO 2014/051165, or the method of the reference process H, the reference process K, or the reference process L each which is described in WO2014/051161.

Reference Process B

The compound (B1) may be prepared by mixing a compound represented by formula (B3) (hereinafter, referred to as Compound (B3)) with pyridine hydrochloride salt followed by heating the resulting mixtures.

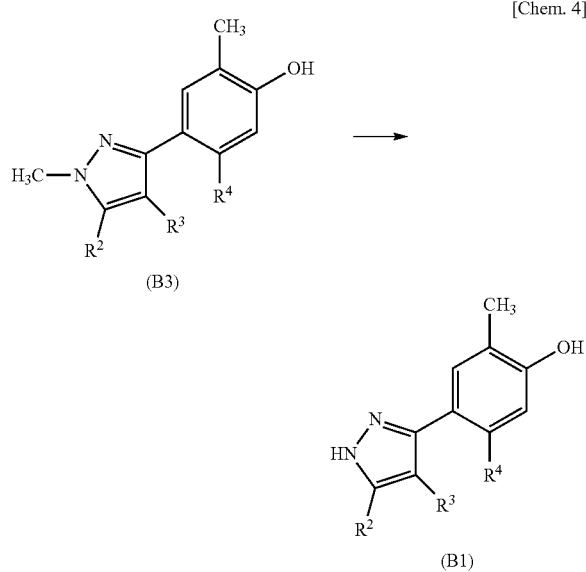

[Chem. 4]

wherein the symbols are the same as defined above.

The pyridine hydrochloride salt is usually used within a range of 1 to 100 molar ratio(s), as opposed to 1 mole of the compound (B3).

The reaction temperature is usually within a range of 150 to 300° C. The heating period of the reaction is usually within a range of 0.1 to 100 hours.

When the reaction is completed, water is added to reaction mixtures, and the reaction mixtures are extracted with organic solvents, and the organic layers are worked up (for example, drying and concentration) to give the compound (B1).

Also the compound (B3) may be prepared by the reference process AE which is described in WO2014/051165, or the reference process B which is described in WO2015/147314.

The control agent of the present invention is usually prepared by mixing the compound of the present invention with solid carrier, liquid carrier, and/or surfactants and the like, and if necessary, adding the other auxiliary agents for formulation such as stickers, dispersers, and stabilizers, to formulate into wettable powders, water dis-persible granules, flowables, granules, dry flowables, emulsifiable concentrates, wettable powders, aqueous solutions, oil solutions, smoking agents, aerosols, micro-capsules and the others. In these formulations, the compound of the present invention is contained in a range of usually 0.1 to 99%, preferably 0.2 to 90% by weight.

Examples of the solid carrier to be used in the formulation include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powder, sulfur powder, activated charcoal, calcium carbonate or hydrated silica).

Examples of the liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles; ethers (for example, diisopropyl ether, 1,4-dioxane, ethyleneglycol dimethyl ether, di-ethyleneglycol dimethyl ether, diethylene glycol monomethyl ether, propylene glycol monomethyl ether, dipropylene glycol monomethyl ether or 3-methoxy-3-methyl-1-butanol); acid amides; and sulfoxides.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of the other auxiliary agents for formulation include stickers, dispersers, and stabilizers. Specific examples include casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), acidic isopropyl phosphate, 2,6-di-tert-butyl-4-methylphenol, BHA (a mixture of 2-tert-butyl-4-methoxyphenol and 3-tert-butyl-4-methoxyphenol), vegetable oils, mineral oils, fatty acids and the others.

Examples of the oil or surfactant to be mixed with the compound of the present invention include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), Agri-Dex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark).

The compound of the present invention may be applied as a control agent of the present invention. The method for applying the present control agent is not particularly limited, as far as the applying form is a form by which the present control agent may be applied substantially, and includes, for example, an application to plants such as a foliage application; an application to area for cultivating plants such as a submerged treatment; and an application to soil such as seed disinfection.

In the control method of the present invention, the application dose of the present compound may be varied depending on a kind of plant to be applied, a kind and a frequency of occurrence of plant diseases to be controlled, a formulation form, an application period, an application method, an application site, a climate condition, and the others. For example, when the compound of the present invention is applied to stems and leaves of plants or soils for cultivating plants, the application dose of the compound of the present invention is within the range of 1 to 500 g per 1,000 $m^2$.

The emulsfiable concentrates, the wettable powders, or flowables etc. are usually applied by diluting them with water, and then spreading them. In this case, the concentration of the present compound is usually 0.0005 to 2% by weight. The dusts or the granules, etc. are usually applied as itself without diluting them.

The compound of the present invention can be used as an agent for controlling plant diseases in an agricultural lands such as fields, paddy fields, lawns, and orchards. The compound of the present invention can control diseases occurred in the agricultural lands or the others in the agricultural lands for cultivating the following "plant" and the like.

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil), strawberry, sweet potato, *Dioscorea japonica, colocasia* and the others;
Flowers:
Ornamental Foliage Plants:
Fruits:
pomaceous fruits (for example, apple, pear, Japanese pear, Chinese quince and quince), stone fruits (for example, peach, plum, nectarine, *Prunus mume*, cherry fruit, apricot and prune),
citrus fruits (for example, Citrus unshiu, orange, lemon, lime and grapefruit), nuts (for example, chestnut, walnuts, hazelnuts, almond, pistachio, cashew nuts and macadamia nuts), berry fruits (for example, blueberry, cranberry, blackberry and raspberry), grape, kaki persimmon, olive, Japanese plum, banana, coffee, date palm, coconuts, and the others;
Trees other than fruit trees:
tea, mulberry, flowering plant,
roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate); and the others.

The above-mentioned "plant" includes genetically modified crops.

Examples of the plant diseases which may be controlled by the present compound include those due to plant pathogens such as filamentous fungi and bacterium, and more specifically include, but are not limited to, the followings. The descriptions in the below-mentioned parenthesis represent a scientific name of the pathogenic bacteria which causes the corresponding plant diseases.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (Blumeriagraminis), fusarium Head blight (*Fusarium graminearum, Fusarium avenaceum, Fusarium culmorum, Microdochium nivale*), yellow rust (*Puccinia striiformis*), black rust (*Puccinia graminis*), red rust (*Puccinia recondita*), snow mold (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off caused by rhizoctonia fungus (*Rhizoctonia solani*), and damping-off (*Gaeumannomyces graminis*);

Barley diseases: powdery mildew (*Blumeria graminis*), loose smut (*Fusarium graminearum, Fusarium avenaceum, Fusarium culmorum, Microdochium nivale*), yellow rust (*Puccinia striiformis*), black rust (*Puccinia graminis*), red rust (*Puccinia hordei*), small rust (*Puccinia hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramuraria leaf spot disease (*Ramularia collo-cygni*), and damping-off caused by rhizoctonia fungus (*Rhizoctonia solani*); Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), Faeosufa area leaf spot disease (*Phaeosphaeria maydis*), Diplodia disease (*Stenocarpella maydis, Stenocarpella macrospora*), stalk rot disease (*Fusarium graminearum, Fusarium verticilioides, Colletotrichum graminicola*), and smut (*Ustilago maydis*);

Cotton diseases: anthracnose (*Colletotrichum gossypii*), Areolate mildew (Ramuraria areola), leaf spot (*Alternaria macrospora, Alternaria gossypii*), and Black root rot caused by *Thielaviopsis* fungus (*Thielaviopsis basicola*); Coffee diseases: rust (*Hemileia vastatrix*) and leaf spot (*Cercospora coffeicola*); Rapeseed diseases: sclerotinia rot (*Sclerotinia sclerotiorum*), alternaria leaf spot (*Alternaria brassicae*), and root rot (*Phoma* lingam);

Sugarcane diseases: rust (*Puccinia* melanocephela, *Puccinia kuehnii*);

Sunflower diseases: rust (*Puccinia helianthi*) and downy mildew (*Plasmopara halstedii*);

Citrus diseases: melanose (*Diaporthe citri*), scab (*Elsinoe fawcetti*), fruit rot (*Penicillium digitatum, Penicillium italicum*), and *Phytophthora* disease (*Phytophthora parasitica, Phytophthora citrophthora*);

Apple diseases: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophthora cactorum*);

Pear diseases: scab (*Venturia nashicola, Venturia pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*);

Diseases of Japanese persimmon: anthracnose (*Gloeosporium kaki*) and leaf spot (*Cercospora kaki*, *Mycosphaerella nawae*);
Diseases of Cucurbitaceae: anthracnose (*Colletotrichum lagenarium*), powdery mildew (*Sphaerotheca fuliginea*), gummy stem blight (*Didymella bryoniae*), corynespora leaf spot (*Corynespora cassiicola*), Fusarium wilt (*Fusarium oxysporum*), downy mildew (*Pseudoperonospora cubensis*), Phytophthora rot (*Phytophthora* sp.), and damping-off (*Pythium* sp.);
Tomato diseases: early blight (*Alternaria solani*), leaf mold (*Cladosporium fulvum*), cercospora leaf mold (*Pseudocercospora fuligena*), late blight (*Phytophthora infestans*), and powdery mildew (*Leveillula taurica*);
Eggplant disease: brown spot (*Phomopsis vexans*) and powdery mildew (*Erysiphe cichoracearum*);
Diseases of *brassica* family: *Alternaria* leaf spot (*Alternaria japonica*), white spot (*Cercosporella brassicae*), clubroot (*Plasmodiophora brassicae*), and downy mildew (*Peronospora parasitica*);
Welsh onion diseases: rust (*Puccinia allii*);
Soybean diseases: purple stain (*Cercospora kikuchii*), Sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (Colletotrithum glycines, *Colletotrichum truncatum*), Rhizoctonia rot (*Rhizoctonia solani*), septoria brown spot (*Septoria glycines*), cercospora leaf spot (*Cercospora sojina*), sclerotinia rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);
Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);
Peanut diseases: leaf spot (*Cercospora personata*), brown leaf spot (*Cercospora arachidicola*), and southern blight (*Sclerotium rolfsii*);
Garden pea diseases: powdery mildew (*Erysiphe pisi*);
Potato diseases: early blight (*Alternaria solani*), late blight (*Phytophthora infestans*), pink rot (*Phytophthora erythroseptica*), powdery scab (*Spongospora subterranea* f. sp. *subterranea*), and *Verticillium* wilt (*Verticillium albo-atrum*, *Verticillium dahliae*, *Verticillium nigrescens*);
Strawberry diseases: powdery mildew (*Sphaerotheca humuli*);
Tea diseases: net blister blight (*Exobasidium reticulatum*), white scab (*Elsinoe leucospila*), gray blight (*Pestalotiopsis* sp.), and anthracnose (*Colletotrichum theae*-sinensis);
Tabacco diseases: brown spot (*Alternaria longipes*), anthracnose (*Colletotrichum tabacum*), downy mildew (*Peronospora tabacina*), and black shank (*Phytophthora nicotianae*);
Sugar beet diseases: cercospora leaf spot (*Cercospora beticola*), leaf blight (*Thanatephorus cucumeris*), root rot (*Thanatephorus cucumeris*), aphanomyces root rot (*Aphanomyces cochlioides*), and rust (*Uromyces betae*);
Rose diseases: blackspot (*Diplocarpon rosae*) and powdery mildew (*Sphaerotheca pannosa*);
Chrysanthemum and Asteraceae vegetable diseases: leaf blight (*Septoria chrysanthemi*-indici) and white rust (*Puccinia horiana*);
Onion diseases: *Botrytis* leaf blight (*Botrytis cinerea*, *B. byssoidea*, *B. squamosa*), neck rot (*Botrytis alli*), and small sclerotial (*Botrytis squamosa*);

Various plants diseases: *Sclerotinia* rot (*Sclerotinia sclerotiorum*);
Japanese radish diseases: *Alternaria* leaf spot (*Alternaria brassicicola*);
Turfgrass diseases: dollar spot (*Sclerotinia homoeocarpa*), and brown patch and large patch (*Rhizoctonia solani*);
Banana diseases: Sigatoka disease (*Mycosphaerella fijiensis*, *Mycosphaerella musicola*);
Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp., and the others; Viral diseases of various plants mediated by *Polymyxa* spp., *Olpidium* spp., or the others; and
Rice bacterial seedling blight (*Burkholderia plantarii*);
, and angular leaf spot (*Pseudomonas syringae* pv. *Lachrymans*);
Eggplant bacterial wilt (*Ralstonia solanacearum*);
Citrus canker (*Xanthomonas citri*);
Chinese cabbage bacterial soft rot (*Erwinia carotovora*); and the others.

EXAMPLES

Hereinafter, the present invention is explained in more detail by using Production examples, Reference Production examples, Formulation examples, and Test examples, however, the present invention should not be limited to these examples. Herein, "Me" represents a methyl group and "Et" represents an ethyl group.

Production Example 1-1

To a mixture of 500 mg of the intermediate compound 1A and 10 mL of DMF was added 0.09 g of sodium hydride (oil, 60%) under ice-cooling, and the mixture was stirred at room temperature for fifteen minutes. To the reaction solution was added dropwise chloromethyl methyl ether 0.9 mL, and the mixture was stirred at room temperature for three hours. To the reaction solution was added water, and the mixture was extracted with MTBE. The obtained organic layer was dried over anhydrous magnesium sulfate and concentrated under reduced pressure. The resulting residue was subjected to silica gel column chromatography (n-hexane:ethyl acetate=1:1) to give the present compound 1 indicated in [Table 1] 0.36 g.

Production Example 1-2

The compounds that were prepared according to the process described in the Production example 1-1 and the physical properties thereof are shown below.
a compound represented by formula (I):

[Chem.5]

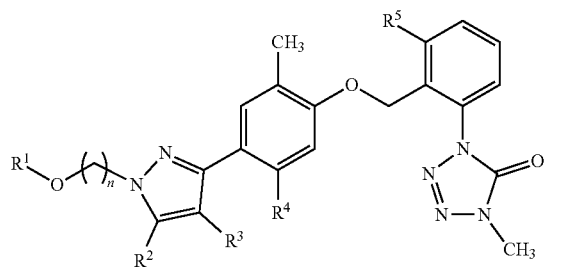

(I)

wherein $R^1$, $R^2$, $R^3$, $R^4$, $R^5$ and n represent any one of the combination indicated in [Table 1].

Here the Present compound 1 represents a compound represented by formula (I) wherein $R^1$, $R^2$, $R^3$, $R^4$, $R^5$ and n represent the combination indicated as Present compound 1 in [Table 1].

For example, Present compound 1 is indicated below.

[Chem.6]

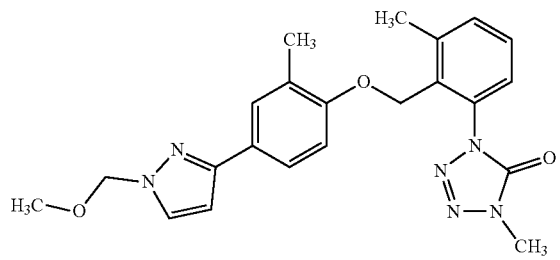

TABLE 1

| Present compound | $R^1$ | $R^2$ | $R^3$ | $R^4$ | $R^5$ | n |
|---|---|---|---|---|---|---|
| 1 | Me | H | H | H | Me | 1 |
| 2 | Me | Me | H | H | Me | 1 |
| 3 | Me | H | Me | H | Me | 1 |
| 4 | Me | H | H | Me | Me | 1 |
| 5 | Me | Me | H | Me | Me | 1 |
| 6 | Et | H | H | H | Me | 1 |
| 7 | Et | Me | H | H | Me | 1 |
| 8 | Et | H | Me | H | Me | 1 |
| 9 | Et | MeF | H | Me | Me | 1 |
| 10 | Me | H | H | H | Me | 2 |
| 11 | Me | Me | H | H | Me | 2 |
| 12 | Me | H | Me | H | Me | 2 |
| 13 | Me | Me | H | Me | Me | 2 |
| 14 | Et | H | H | H | Me | 2 |
| 15 | Et | Me | H | Me | Me | 2 |
| 16 | Me | Me | H | Me | H | 1 |
| 17 | Et | Me | H | Me | H | 1 |
| 18 | Me | Cl | H | H | Me | 1 |
| 19 | Et | Cl | H | H | Me | 1 |
| 20 | Me | Cl | H | H | Me | 2 |
| 21 | Me | F | Me | H | Me | 1 |
| 22 | Et | F | Me | H | Me | 1 |
| 23 | Me | F | H | 1 H | Me | 1 |
| 24 | Et | F | H | H | Me | 1 |

Present compound 1:
$^1$H-NMR (CDCl$_3$) δ: 7.61 (1H, s), 7.58-7.56 (2H, m), 7.43-7.41 (2H, m), 7.30-7.27 (1H, m), 6.87 (1H, d, J=8.2 Hz), 6.56 (1H, d, J=2.3 Hz), 5.41 (2H, s), 5.07 (2H, s), 3.62 (3H, s), 3.37 (3H, s), 2.51 (3H, s), 2.13 (3H, s).

Present compound 2:
$^1$H-NMR (CDCl$_3$) δ: 7.58-7.55 (1H, m), 7.52 (1H, dd, J=8.5, 2.3 Hz), 7.42-7.41 (2H, m), 7.29-7.28 (1H, m), 6.85 (1H, d, J=8.5 Hz), 6.32 (1H, s), 5.39 (2H, s), 5.06 (2H, s), 3.62 (3H, s), 3.35 (3H, s), 2.51 (3H, s), 2.37 (3H, s), 2.12 (3H, s).

Present compound 3:
$^1$H-NMR (CDCl$_3$) δ: 7.48-7.47 (1H, m), 7.45-7.38 (4H, m), 7.29-7.27 (1H, m), 6.89 (1H, d, J=8.4 Hz), 5.35 (2H, s), 5.07 (2H, s), 3.63 (3H, s), 3.36 (3H, s), 2.51 (3H, s), 2.22 (3H, s), 2.13 (3H, s).

Present compound 4:
$^1$H-NMR (CDCl$_3$) δ: 7.58-7.57 (1H, m), 7.43-7.38 (2H, m), 7.32 (1H, s), 7.28-7.26 (1H, m), 6.71 (1H, s), 6.43 (1H, s), 5.42 (2H, s), 5.06 (2H, s), 3.64 (3H, s), 3.37 (3H, s), 2.51 (3H, s), 2.43 (3H, s), 2.08 (3H, s).

Present compound 5:
$^1$H-NMR (CDCl$_3$) δ: 7.44-7.39 (2H, m), 7.28-7.26 (2H, m), 6.69 (1H, s), 6.18 (1H, s), 5.40 (2H, s), 5.04 (2H, s), 3.64 (3H, s), 3.35 (3H, s), 2.51 (3H, s), 2.41 (3H, s), 2.38 (3H, s), 2.06 (3H, s).

Present compound 6:
$^1$H-NMR (CDCl$_3$) δ: 7.60 (1H, s), 7.57-7.55 (2H, m), 7.44-7.39 (2H, m), 7.29-7.27 (1H, m), 6.86 (1H, d, J=8.4 Hz), 6.54 (1H, d, J=2.3 Hz), 5.45 (2H, s), 5.07 (2H, s), 3.62 (3H, s), 3.58 (2H, q, J=7.0 Hz), 2.51 (3H, s), 2.13 (3H, s), 1.18 (3H, t, J=7.0 Hz).

Present compound 7:
$^1$H-NMR (CDCl$_3$) δ: 7.55 (1H, s), 7.51 (1H, d, J=8.8 Hz), 7.46-7.37 (2H, m), 7.31-7.27 (1H, m), 6.85 (1H, d, J=8.6 Hz), 6.30 (1H, s), 5.43 (2H, s), 5.06 (2H, s), 3.61 (3H, s), 3.56 (2H, q, J=7.0 Hz), 2.51 (3H, s), 2.37 (3H, s), 2.12 (3H, s), 1.16 (3H, t, J=7.0 Hz).

Present compound 8:
$^1$H-NMR (CDCl$_3$) δ: 7.47-7.46 (1H, m), 7.44-7.38 (4H, m), 7.29-7.27 (1H, m), 6.88 (1H, d, J=8.4 Hz), 5.39 (2H, s), 5.07 (2H, s), 3.63 (3H, s), 3.57 (2H, q, J=7.0 Hz), 2.51 (3H, s), 2.22 (3H, s), 2.13 (3H, s), 1.18 (3H, t, J=7.0 Hz).

Present compound 9:
$^1$H-NMR (CDCl$_3$) δ: 7.44-7.39 (2H, m), 7.28-7.27 (2H, m), 6.69 (1H, s), 6.17 (1H, s), 5.45 (2H, s), 5.04 (2H, s), 3.64 (3H, s), 3.57 (2H, q, J=7.1 Hz), 2.51 (3H, s), 2.41 (3H, s), 2.39 (3H, s), 2.06 (3H, s), 1.17 (3H, t, J=7.0 Hz).

Present compound 10:
$^1$H-NMR (CDCl$_3$) δ: 7.57 (1H, d, J=1.4 Hz), 7.54-7.51 (1H, m), 7.46 (1H, d, J=2.3 Hz), 7.44-7.39 (2H, m), 7.29-7.26 (1H, m), 6.85 (1H, d, J=8.4 Hz), 6.45 (1H, d, J=2.3 Hz), 5.06 (2H, s), 4.31 (2H, t, J=5.3 Hz), 3.78 (2H, t, J=5.3 Hz), 3.62 (3H, s), 3.34 (3H, s), 2.51 (3H, s), 2.12 (3H, s).

Present compound 11:
$^1$H-NMR (CDCl$_3$) δ: 7.54-7.53 (1H, m), 7.50-7.47 (1H, m), 7.44-7.39 (2H, m), 7.28-7.27 (1H, m), 6.84 (1H, d, J=8.6 Hz), 6.21 (1H, s), 5.05 (2H, s), 4.21 (2H, t, J=5.5 Hz), 3.77 (2H, t, J=5.5 Hz), 3.61 (3H, s), 3.31 (3H, s), 2.51 (3H, s), 2.32 (3H, s), 2.11 (3H, s).

Present compound 12:
$^1$H-NMR (CDCl$_3$) δ: 7.47-7.39 (4H, m), 7.30-7.27 (2H, m), 6.87 (1H, d, J=8.4 Hz), 5.06 (2H, s), 4.25 (2H, t, J=5.3 Hz), 3.76 (2H, t, J=5.3 Hz), 3.62 (3H, s), 3.35 (3H, s), 2.51 (3H, s), 2.19 (3H, s), 2.12 (3H, s).

Present compound 13:
$^1$H-NMR (CDCl$_3$) δ: 7.43-7.38 (2H, m), 7.29-7.26 (2H, m), 6.69 (1H, s), 6.08 (1H, s), 5.04 (2H, s), 4.22 (2H, t, J=5.7 Hz), 3.78 (2H, t, J=5.7 Hz), 3.64 (3H, s), 3.31 (3H, s), 2.50 (3H, s), 2.42 (3H, s), 2.33 (3H, s), 2.06 (3H, s).

Present compound 14:
$^1$H-NMR (CDCl$_3$) δ: 7.58-7.57 (1H, m), 7.54-7.52 (1H, m), 7.48 (1H, d, J=2.3 Hz), 7.44-7.39 (2H, m), 7.28-7.27 (1H, m), 6.85 (1H, d, J=8.4 Hz), 6.44 (1H, d, J=2.3 Hz), 5.06 (2H, s), 4.31 (2H, t, J=5.3 Hz), 3.81 (2H, t, J=5.3 Hz), 3.62 (3H, s), 3.46 (2H, q, J=7.0 Hz), 2.51 (3H, s), 2.12 (3H, s), 1.16 (3H, t, J=7.0 Hz).

Present compound 15:
$^1$H-NMR (CDCl$_3$) δ: 7.44-7.38 (2H, m), 7.29-7.26 (2H, m), 6.69 (1H, s), 6.07 (1H, s), 5.04 (2H, s), 4.22 (2H, t, J=5.8 Hz), 3.81 (2H, t, J=5.8 Hz), 3.64 (3H, s), 3.44 (2H, q, J=7.0 Hz), 2.50 (3H, s), 2.41 (3H, s), 2.34 (3H, s), 2.06 (3H, s), 1.14 (3H, t, J=7.0 Hz).

Present compound 16:
$^1$H-NMR (CDCl$_3$) δ: 7.72 (1H, d, J=7.1 Hz), 7.56-7.47 (3H, m), 7.30 (1H, s), 6.66 (1H, s), 6.18 (1H, s), 5.40 (2H, s), 5.16 (2H, s), 3.69 (3H, s), 3.36 (3H, s), 2.39 (3H, s), 2.38 (3H, s), 2.16 (3H, s).

Present compound 17:

¹H-NMR (CDCl₃) δ: 7.72 (1H, d, J=7.1 Hz), 7.56-7.47 (3H, m), 7.29 (1H, s), 6.66 (1H, s), 6.16 (1H, s), 5.45 (2H, s), 5.16 (2H, s), 3.69 (3H, s), 3.58 (2H, q, J=7.0 Hz), 2.39 (6H, s), 2.16 (3H, s), 1.17 (3H, t, J=7.0 Hz).

Present compound 18:

¹H-NMR (CDCl₃) δ: 7.56-7.55 (1H, m), 7.51 (1H, dd, J=8.5, 2.3 Hz), 7.45-7.39 (2H, m), 7.29-7.26 (1H, m), 6.86 (1H, d, J=8.5 Hz), 6.50 (1H, s), 5.45 (2H, s), 5.07 (2H, s), 3.62 (3H, s), 3.41 (3H, s), 2.51 (3H, s), 2.12 (3H, s).

Present compound 19:

¹H-NMR (CDCl₃) δ: 7.55 (1H, s), 7.52-7.49 (1H, m), 7.46-7.38 (2H, m), 7.31-7.27 (1H, m), 6.86 (1H, d, J=8.6 Hz), 6.49 (1H, s), 5.49 (2H, s), 5.07 (2H, s), 3.66-3.61 (5H, m), 2.51 (3H, s), 2.13 (3H, s), 1.20 (3H, t, J=7.0 Hz).

Present compound 20:

¹H-NMR (CDCl₃) δ: 7.52 (1H, s), 7.48 (1H, dd, J=8.4, 2.3 Hz), 7.44-7.39 (2H, m), 7.30-7.28 (1H, m), 6.85 (1H, d, J=8.4 Hz), 6.41 (1H, s), 5.06 (2H, s), 4.32 (2H, t, J=5.9 Hz), 3.81 (2H, t, J=5.9 Hz), 3.62 (3H, s), 3.35 (3H, s), 2.51 (3H, s), 2.12 (3H, s).

Present compound 21:

¹H-NMR (CDCl₃) δ: 7.47-7.41 (2H, m), 7.29 (1H, dd, J=7.0, 2.4 Hz), 7.23-7.20 (1H, m), 7.17-7.16 (1H, m), 6.92 (1H, d, J=8.5 Hz), 5.12 (2H, s), 5.07 (2H, s), 3.66 (3H, s), 3.40 (3H, s), 2.53 (3H, s), 2.13 (3H, s), 1.94 (3H, s).

Present compound 22:

¹H-NMR (CDCl₃) δ: 7.47-7.42 (2H, m), 7.29 (1H, dd, J=6.9, 2.3 Hz), 7.24 (1H, dd, J=8.5, 2.3 Hz), 7.18 (1H, d, J=2.3 Hz), 6.93 (1H, d, J=8.2 Hz), 5.16 (2H, s), 5.08 (2H, s), 3.66-3.60 (5H, m), 2.53 (3H, s), 2.13 (3H, s), 1.94 (3H, s), 1.18 (3H, t, J=7.1 Hz).

Present compound 23:

¹H-NMR (CDCl₃) δ: 7.56-7.55 (1H, m), 7.50 (1H, dd, J=8.4, 1.8 Hz), 7.45-7.39 (2H, m), 7.29-7.26 (1H, m), 6.85 (1H, d, J=8.6 Hz), 6.02 (1H, d, J=5.7 Hz), 5.34 (2H, s), 5.07 (2H, s), 3.62 (3H, s), 3.41 (3H, s), 2.51 (3H, s), 2.12 (3H, s).

Present compound 24:

¹H-NMR (CDCl₃) δ: 7.54 (1H, s), 7.49 (1H, d, J=8.4 Hz), 7.44-7.39 (2H, m), 7.28-7.27 (1H, m), 6.85 (1H, d, J=8.6 Hz), 6.01 (1H, d, J=5.4 Hz), 5.38 (2H, s), 5.06 (2H, s), 3.66-3.61 (5H, m), 2.51 (3H, s), 2.12 (3H, s), 1.20 (3H, t, J=7.0 Hz).

Production Example 2-1

A mixture 0.47 g of the present compound 1, 0.14 g of N-chlorosuccinimide and 2.5 mL of DMF was stirred at 40° C. for two hours. To the reaction solution was added water, and the mixture was extracted with MTBE. The obtained organic layer was dried over anhydrous magnesium sulfate and concentrated under reduced pressure. The resulting residue was subjected to silica gel column chromatography (n-hexane:ethyl acetate=1:1) to give 0.36 g of the present compound 25 indicated in Table 2.

Production Example 2-2

The compounds that were prepared according to the process described in the Production example 2-1 and the physical properties thereof are shown below. Examples thereof include a compound represented by formula (I) wherein R¹, R², R³, R⁴, R⁵ and n represent any one of the combinations indicated in Table 2.

Present compound 25 is indicated below.

[Chem.7]

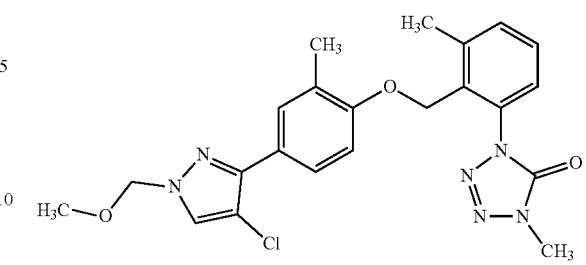

TABLE 2

| Present compound | R¹ | R² | R³ | R⁴ | R⁵ | n |
|---|---|---|---|---|---|---|
| 25 | Me | H | Cl | H | Me | 1 |
| 26 | Et | Me | Cl | H | Me | 1 |

Present compound 25:

¹H-NMR (CDCl₃) δ: 7.69 (1H, dd, J=8.4, 2.3 Hz), 7.66-7.64 (1H, m), 7.62 (1H, s), 7.45-7.40 (2H, m), 7.28 (1H, dd, J=6.8, 2.5 Hz), 6.90 (1H, d, J=8.4 Hz), 5.35 (2H, s), 5.08 (2H, s), 3.63 (3H, s), 3.37 (3H, s), 2.51 (3H, s), 2.14 (3H, s).

Present compound 26:

¹H-NMR (CDCl₃) δ: 7.46-7.41 (2H, m), 7.36 (1H, d, J=8.4 Hz), 7.32 (1H, s), 7.30-7.28 (1H, m), 6.95 (1H, d, J=8.6 Hz), 5.25 (2H, s), 5.08 (2H, s), 3.66-3.60 (5H, m), 2.53 (3H, s), 2.29 (3H, s), 2.14 (3H, s), 1.19 (3H, t, J=7.0 Hz).

Production Example 3

A mixture of 0.59 g of the present compound 2, 0.23 g of N-bromosuccinimide and 3 mL of chloroform was stirred at room temperature for one hour. To the reaction solution was added water, and the mixture was extracted with chloroform. The obtained organic layer was dried over anhydrous magnesium sulfate and concentrated under reduced pressure. The resulting residue was subjected to silica gel column chromatography (n-hexane:ethyl acetate=1:1) to give 0.5 g of the present compound 27 below.

[Chem.8]

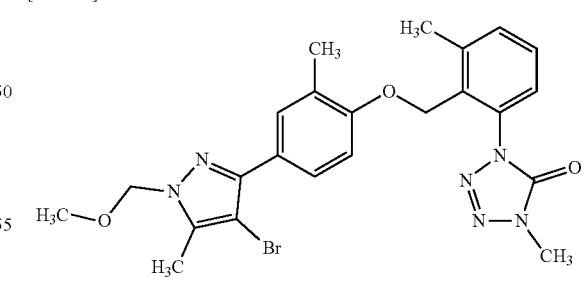

¹H-NMR (CDCl₃) δ: 7.66 (1H, d, J=8.5 Hz), 7.60 (1H, s), 7.46-7.39 (2H, m), 7.33-7.27 (1H, m), 6.90 (1H, d, J=8.5 Hz), 5.41 (2H, s), 5.07 (2H, s), 3.63 (3H, s), 3.35 (3H, s), 2.51 (3H, s), 2.38 (3H, s), 2.13 (3H, s).

Production Example 4

A mixture of 0.5 g of the present compound 27, 0.23 g of methylboronic acid, 1.27 g of cesium fluoride, 0.08 g of

[1,1'-bis(diphenylphosphino)ferrocene]palladium(II) dichloride dichloromethane adduct, and 5 mL of 1,2-dimethoxyethane was heated under reflux for two hours with stirring. The reaction solution was filtered through Celite (registered trademark) and the filtrate was concentrated under reduced pressure. The resulting residue was subjected to a silica gel column chromatography (n-hexane:ethyl acetate=1:1) to give 0.5 g of the present compound 28 below.

[Chem.9]

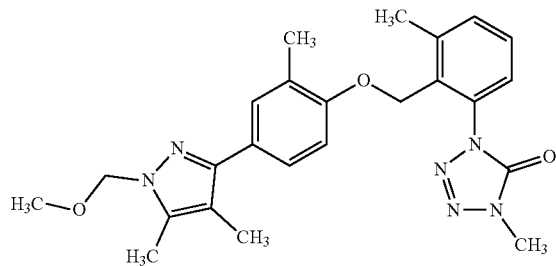

$^1$H-NMR (CDCl$_3$) δ: 7.43-7.37 (4H, m), 7.29-7.27 (1H, m), 6.88 (1H, d, J=8.5 Hz), 5.38 (2H, s), 5.06 (2H, s), 3.63 (3H, s), 3.33 (3H, s), 2.51 (3H, s), 2.28 (3H, s), 2.13 (3H, s), 2.11 (3H, s).

Next, the reference Production examples for preparing Production intermediate of the above-mentioned present compounds are described.

Reference Production Example 1-1

To a mixture of 10 g of the intermediate compound 8A and 40 mL of ethanol was added 8.5 mL of hydrazine monohydrate and the mixture was stirred at room temperature overnight. The reaction solution was concentrated under reduced pressure, and the resulting residue was washed with hexane, successively with a mixed solution of hexane:MTBE=10:1 to give 16.2 g of the intermediate compound 2A indicated in [Table 3].

Reference Production Example 1-2

The compounds that were prepared according to the process described in the Reference Production example 1-1 and the physical properties thereof are shown below.

a compound represented by formula (aA):

[Chem.10]

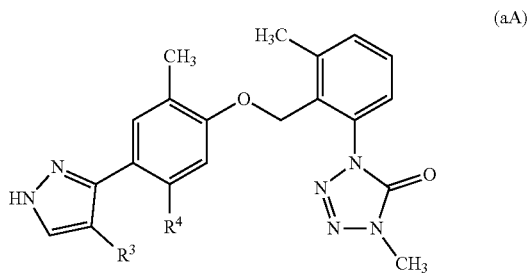

(aA)

wherein R$^3$ and R$^4$ represent any one of the combinations indicated in [Table 3].

TABLE 3

| Intermediate compound | R$^3$ | R$^4$ |
|---|---|---|
| 1A | H | H |
| 2A | H | Me |

Intermediate compound 1A:
$^1$H-NMR (CDCl$_3$) δ: 7.58 (1H, s), 7.48 (2H, d, J=6.4 Hz), 7.43 (2H, t, J=7.6 Hz), 7.28 (1H, d, J=2 Hz), 6.87 (1H, d, J=9.2 Hz), 6.51 (1H, s), 5.07 (2H, s), 3.61 (3H, s), 2.51 (3H, s), 2.13 (3H, s).

Intermediate compound 2A:
$^1$H-NMR (CDCl$_3$) δ: 7.62 (1H, d, J=2.0 Hz), 7.43 (2H, m), 7.29 (1H, m), 7.19 (1H, s), 6.73 (1H, s), 6.37 (1H, d, J=1.8 Hz), 5.06 (2H, s), 3.65 (3H, s), 2.52 (3H, s), 2.39 (3H, s), 2.08 (3H, s).

Reference Production Example 2

A mixture of 10 g of the intermediate compound 6A and 18 mL of N,N-dimethylformamide diethyl acetal was heated under reflux for twenty four hours with stirring. The reaction solution was concentrated under reduced pressure, and thereto were 30 mL of ethanol and 5 mL of hydrazine monohydrate, and the mixture was stirred at room temperature for six hours. The mixture was concentrated under reduced pressure and the resulting residue was subjected to a silica gel column chromatography to give 5.5 g of the intermediate compound 3A below.

[Chem.11]

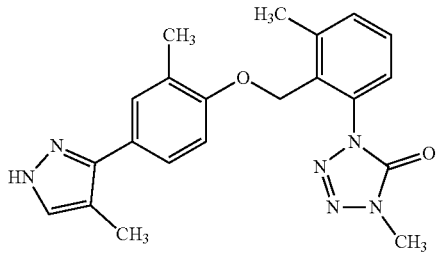

$^1$H-NMR (CDCl$_3$) δ: 7.46-7.40 (3H, m), 7.32 (2H, s), 7.28 (1H, dd, J=7.0, 2.5 Hz), 6.91 (1H, d, J=9.1 Hz), 5.08 (2H, s), 3.63 (3H, s), 2.52 (3H, s), 2.21 (3H, s), 2.14 (3H, s).

Reference Production Example 3-1

A mixture of 15.0 g of 1-(2,5-dimethyl-4-hydroxyphenyl)ethanone, 25 g of 1-{2-(bromomethyl)-3-methylphenyl}-4-methyl-4,5-dihydrotetrazol-5-one, 18 g of potassium carbonate, and 130 mL of acetonitrile was heated under reflux for five hours with stirring. The reaction solution was filtered through Celite (registered trademark) and the filtrate was concentrated under reduced pressure. To the resulting residue was added ethyl acetate, and the mixture was washed with saturated sodium hydrogen sulfate solution. The organic layer was dried over anhydrous magnesium sulfate and concentrated under reduced pressure to give 29.0 g of the intermediate compound 5A indicated in [Table 4].

Reference Production Example 3-2

The compounds that were prepared according to the process described in the Reference Production example 3-1 and the physical properties thereof are shown below.

a compound represented by formula (bA):

[Chem.12]

(bA)

wherein $R^4$ and $R^6$ represent any one of the combinations indicated in [Table 4].

TABLE 4

| Intermediate compound | $R^4$ | $R^6$ |
|---|---|---|
| 4A | H | H |
| 5A | Me | H |
| 6A | H | Me |

Intermediate compound 4A:

$^1$H-NMR (CDCl$_3$) δ: 7.80-7.75 (2H, m), 7.46-7.40 (2H, m), 7.28 (1H, dd, J=2, 7.6 Hz), 6.86 (1H, d, J=8.8 Hz), 5.11 (2H, s), 3.62 (3H, s), 2.54 (3H, s), 2.50 (3H, s), 2.12 (3H, s).

Intermediate compound 5A:

$^1$H-NMR (CDCl$_3$) δ: 7.53 (1H, s), 7.46-7.40 (2H, m), 7.28 (1H, dd, J=7.2, 2.3 Hz), 6.66 (1H, s), 5.08 (2H, s), 3.64 (3H, s), 2.55 (3H, s), 2.53 (3H, s), 2.50 (3H, s), 2.09 (3H, s).

Intermediate compound 6A:

$^1$H-NMR (CDCl$_3$) δ: 7.80 (1H, d, J=8.5 Hz), 7.77-7.74 (1H, m), 7.45-7.41 (2H, m), 7.29 (1H, d, J=7.3 Hz), 6.86 (1H, d, J=8.5 Hz), 5.11 (2H, s), 3.62 (3H, s), 2.94 (2H, q, J=7.3 Hz), 2.50 (3H, s), 2.12 (3H, s), 1.20 (3H, t, J=7.3 Hz).

Reference Production Example 4-1

A mixture of 10 g of the intermediate compound 5A and 14 mL of N,N-dimethylformamide diethyl acetal was heated under reflux with stirring for twenty four hours. The reaction solution was concentrated under reduced pressure to give the intermediate compound 8A indicated in [Table 5].

Reference Production Example 4-2

The compounds that were prepared according to the process described in the Reference Production example 4-1 and the physical properties thereof are shown below.

a compound represented by formula (cA):

[Chem.13]

(cA)

wherein $R^4$ and $R^5$ represent any one of the combinations indicated in [Table 5]

TABLE 5

| Intermediate compound | $R^4$ | $R^7$ |
|---|---|---|
| 7A | H | H |
| 8A | Me | H |

Intermediate compound 7A:

$^1$H-NMR (CDCl$_3$) δ: 7.79-7.71 (3H, m), 7.59-7.39 (2H, m), 7.31-7.28 (1H, m), 6.84 (1H, d, J=8.4 Hz), 5.69 (1H, d, J=12.4 Hz), 5.09 (2H, s), 3.63 (3H, s), 3.03-2.88 (6H, m), 2.50 (3H, s), 2.09 (3H, s).

Intermediate compound 8A:

$^1$H-NMR (CDCl$_3$) δ: 7.46-7.40 (3H, m), 7.27 (1H, dd, J=6.7, 2.6 Hz), 7.14 (1H, s), 6.64 (1H, s), 5.35 (1H, d, J=12.7 Hz), 5.04 (2H, s), 3.65 (3H, s), 3.08 (3H, s), 2.88 (3H, s), 2.51 (3H, s), 2.39 (3H, s), 1.88 (3H, s).

Reference Production Example 5

To a mixture of 10 g of the intermediate compound 4A and 95 mL of THF was added 2.6 g of sodium hydride (oil, 60%), and the mixture was stirred at room temperature for thirty minutes. To the mixture was added 0.2 g of dibenzo-18-crown-6 and 7 mL of ethyl acetate, and the mixture was heated under reflux for four hours. To the reaction mixture was added water, and the mixture was acidified with 3N hydrochloric acid. The mixture was extracted with ethyl acetate and the obtained organic layer was dried over anhydrous magnesium sulfate and concentrated under reduced pressure. The resulting residue was subjected to silica gel column chromatography to give the intermediate compound 10A below.

[Chem.14]

$^1$H-NMR (CDCl$_3$) δ: 7.72 (1H, dd, J=8.5, 2.2 Hz), 7.67-7.66 (1H, m), 7.46-7.40 (2H, m), 7.29 (1H, dd, J=7.1, 1.9

Hz), 6.88 (1H, d, J=8.5 Hz), 6.11 (1H, s), 5.11 (2H, s), 4.81 (1H, s), 3.62 (3H, s), 2.50 (3H, s), 2.17 (3H, s), 2.12 (3H, s).

Reference Production Example 6

To a mixture of 10 g of the intermediate compound 10A and 30 mL of ethanol was added 5 mL of hydrazine monohydrate, and the mixture was stirred at room temperature for one hour. The reaction solution was concentrated under reduced pressure. The resulting residue was washed with hexane and successively with a mixed solution consisting of hexane:MTBE=10:1 to give the intermediate compound 12 A below.

[Chem.15]

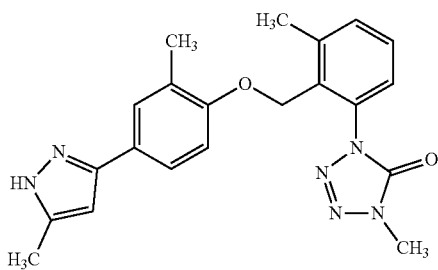

$^1$H-NMR (CDCl$_3$) δ: 7.45-7.42 (4H, m), 7.28-7.27 (1H, m), 6.86 (1H, d, J=8.9 Hz), 6.26 (1H, s), 5.06 (2H, s), 3.61 (3H, s), 2.51 (3H, s), 2.33 (3H, s), 2.12 (3H, s).

Reference Production Example 7

To a mixture of 10 g of the intermediate compound 5A and 100 mL of THF was added 2.5 g of sodium hydride (oil, 60%) under ice-cooling, and the mixture was stirred at room temperature for thirty minutes. To the mixture was added 0.02 g of dibenzo-crown-6 and 4.8 g of ethyl acetate, and the mixture was heated under reflux with stirring at 40° C. Thereafter, to the reaction mixture was added dropwise 1.4 g of ethanol slowly, and the mixture was heated under reflux with stirring for six hours. To the reaction mixture was added water, and the mixture was extracted with ethyl acetate, and the obtained organic layer was dried over anhydrous sodium sulfate and concentrated under reduced pressure. To the resulting residue was added 50 mL of ethanol and 1.6 g of hydrazine monohydrate, and the mixture was stirred for one hour. The resulting residue was washed with hexane, and successively with a mixed solution consisting of hexane:MTBE=10:1 to give the intermediate compound 13A below.

[Chem.16]

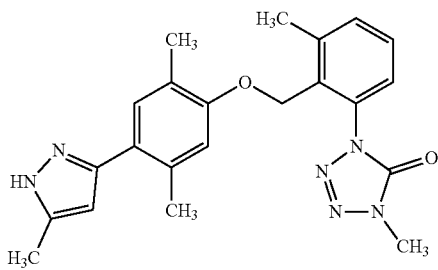

$^1$H-NMR (CDCl$_3$) δ: 7.43-7.41 (2H, m), 7.29-7.28 (1H, m), 7.18-7.15 (1H, m), 6.71 (1H, s), 6.13 (1H, s), 5.05 (2H, s), 3.65 (3H, s), 2.52 (3H, s), 2.38 (3H, s), 2.35 (3H, s), 2.07 (3H, s).

Reference Production Example 8

A mixture of 100 g of 5-chloro-4-formyl-3-(4-methoxy-3-methylphenyl)-1-methyl-1H-pyrazole, 600 mL of toluene and 480 mL of sulfone was heated with stirring in 150° C. oil bath, and the toluene was evaporated off. The mixture was cooled to room temperature, and thereafter, the reactor was purged with nitrogen gas, and thereto was added 55 g of potassium fluoride. The reactor was immersed in 150° C. oil bath again, and all toluene was evaporated off. Thereafter, the mixture was heated to 200° C. and stirred for three hours. The reaction mixture was cooled to room temperature and thereto was added water, and the mixture was extracted with ethyl acetate. The resulting mixture was washed with saturated brine, dried over anhydrous magnesium sulfate, and concentrated under reduced pressure. The resulting residue was subjected to silica gel column chromatography to give 61 g of the intermediate compound 14A below.

[Chem.17]

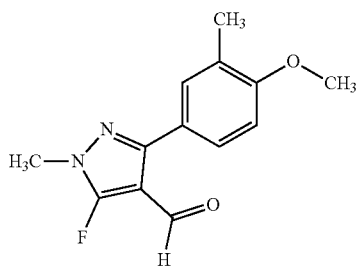

$^1$H-NMR (CDCl$_3$) δ: 9.85 (1H, s), 7.56 (1H, dd, J=8.4, 2.3 Hz), 7.52 (1H, d, J=2.3 Hz), 6.90 (1H, d, J=8.4 Hz), 3.88 (3H, s), 3.82 (3H, s), 2.27 (3H, s).

Reference Production Example 9

To a mixture of 93 g of the intermediate compound 14A and 436 g of trifluoroacetic acid was added dropwise 109 g of triethylsilane over 40 minutes under ice-cooling. The mixture was heated with stirring for six hours, and concentrated under reduced pressure. To the resulting residue was added water 200 mL, and the mixture was added sodium carbonate under ice-cooling to make pH=8. The mixture was extracted with ethyl acetate, and the obtained organic layer was washed with water, dried over anhydrous magnesium sulfate and concentrated under reduced pressure. To the resulting residues were added 450 g of acetic acid and 970 g of 47% hydrobromic acid successively and the mixture was stirred at 100° C. for ten hours. The reaction solution was concentrated under reduced pressure to about a half volume thereof. To the reaction solution was added 3N aqueous sodium hydroxide solution to make pH=7 to 8, and the mixture was extracted with ethyl acetate. The obtained organic layer was washed with water, dried over anhydrous magnesium sulfate, and concentrated under reduced pressure. The obtained residue was subjected to silica gel column chromatography to give 52.49 g of the intermediate compound 15A below.

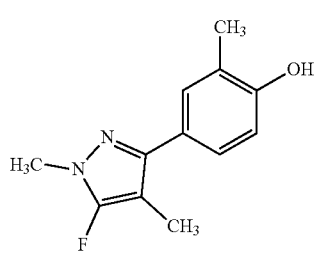

[Chem.18]

¹H-NMR (CDCl₃) δ: 7.43 (1H, s), 7.32 (1H, d, J=7.9 Hz), 6.80 (1H, d, J=7.9 Hz), 4.83 (1H, d, J=5.9 Hz), 3.74 (3H, s), 2.29 (3H, s), 2.09 (3H, s).

Reference Production Example 10-1

A mixture of 3 g of 5-chloro-3-(4-hydroxy-3-methylphenyl)-1-methyl-1H-pyrazole and 7.8 g of pyridine hydrochloride salt was heated at 200° C. with stirring for two hours. The resulting mixture was cooled to room temperature, and thereto was added water, and the mixture was extracted with ethyl acetate. The obtained organic layer was dried over anhydrous magnesium sulfate and concentrated under reduced pressure. The obtained residue was subjected to silica gel column chromatography to give 1.92 g of the intermediate compound 16A indicated in [Table 6].

Reference Production Example 10-2

The compounds that were prepared according to the process described in the Reference Production example 1-1 and the physical properties thereof are shown below.
a compound represented by formula (fA):

[Chem.19]

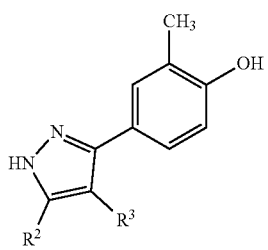

(fA)

wherein R² and R³ represent any one of the combinations indicated in [Table 6].

TABLE 6

| Intermediate compound | R² | R³ |
|---|---|---|
| 16A | Cl | H |
| 19A | F | Me |
| 20A | F | H |

Intermediate compound 16A:
¹H-NMR (CDCl₃) δ: 7.30-7.28 (1H, m), 7.24 (1H, dd, J=8.4, 2.2 Hz), 6.84 (1H, d, J=8.4 Hz), 6.36 (1H, s), 2.30 (3H, s).

Intermediate compound 19A:
¹H-NMR (CDCl₃) δ: 7.21 (1H, s), 7.17 (1H, d, J=8.2 Hz), 6.87 (1H, d, J=8.4 Hz), 2.31 (3H, s), 2.13 (3H, s).

Intermediate compound 20A:
¹H-NMR (CDCl₃) δ: 7.28 (1H, s), 7.24 (1H, d, J=8.2 Hz), 6.84 (1H, d, J=8.4 Hz), 5.99 (1H, d, J=5.9 Hz), 2.30 (3H, s).

Reference Production Example 11

To a mixture of 21.9 g of sodium chlorite, 37.2 g of sodium dihydrogen phosphate dihydrate, 68 mL of 2-methyl-2-butene, 100 mL of THF, 100 mL of tert-butyl alcohol and 33 mL of water was added 20 g of the intermediate compound 14A under ice-cooling, and the mixtures were stirred at room temperature for one hour. The reaction solution was concentrated under reduced pressure, and to the resulting residue was added water, and the mixture was extracted with ethyl acetate. The obtained organic layer was washed with 1N hydrochloric acid and saturated brine successively, dried over anhydrous magnesium sulfate, and concentrated under reduced pressure. The obtained solid was washed with hexane to give 19.32 g of the intermediate compound 17A below.

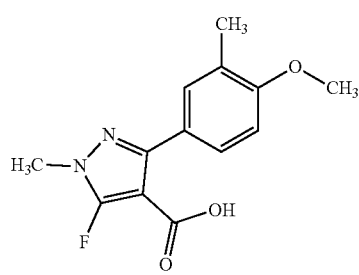

[Chem.20]

¹H-NMR (CDCl₃) δ: 7.52 (1H, dd, J=8.4, 2.3 Hz), 7.46 (1H, d, J=2.3 Hz), 6.85 (1H, d, J=8.4 Hz), 3.86 (3H, s), 3.80 (3H, s), 2.24 (3H, s).

Reference Production Example 12

A mixture of 5 g of the intermediate compound 17A, 30 mL of acetic acid and 30 mL of 47% hydrobromic acid was heated at 110° C. with stirring for eight hours. The reaction solution was cooled under ice, and thereto was added 2N aqueous sodium hydroxide solution to make pH=9. The mixture was extracted with ethyl acetate and the obtained organic layer was dried over anhydrous magnesium sulfate, and concentrated under reduced pressure. The resulting residue was subjected to silica gel column chromatography to give 1.60 g of the intermediate compound 18A below.

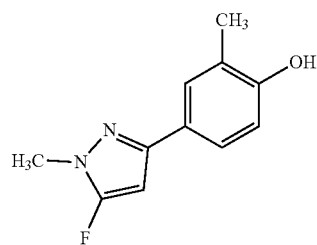

[Chem.21]

¹H-NMR (CDCl₃) δ: 7.52 (1H, d, J=1.4 Hz), 7.42-7.39 (1H, m), 6.78 (1H, d, J=8.2 Hz), 5.95 (1H, d, J=5.7 Hz), 5.03 (1H, s), 3.76 (3H, d, J=1.1 Hz), 2.28 (3H, s).

Reference Production Example 13-1

A mixture of 1.92 g of the intermediate compound 16A, 2.48 g of 1-[2-(bromomethyl)-3-methylphenyl]-4-methyl-4,5-dihydrotetrazole-5-one, 1.91 g of potassium carbonate, and 37 mL of acetonitrile was heated under reflux with stirring for four hours. The reaction solution was filtered through Celite (registered trademark), and the filtrate was concentrated under reduced pressure. The resulting residue was subjected to silica gel column chromatography to give 0.99 g of the intermediate compound 21A indicated in [Table 7].

Reference Production Example 13-2

The compounds that were prepared according to the process described in the Reference Production example 13-1 and the physical properties thereof are shown below.
a compound represented by formula (gA):

[Chem.22]

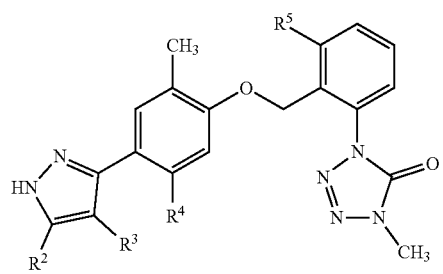

(gA)

wherein $R^2$, $R^3$, $R^4$ and $R^5$ represent any one of the combinations indicated in [Table 7].

TABLE 7

| Intermediath compound | $R^2$ | $R^3$ | $R^4$ | $R^5$ |
|---|---|---|---|---|
| 21A | Cl | H | H | Me |
| 22A | F | Me | H | Me |
| 23A | F | H | H | Me |
| 24A | Me | H | Me | H |

Intermediate compound 21A:
$^1$H-NMR (CDCl$_3$) δ: 7.43-7.42 (1H, m), 7.38-7.33 (3H, m), 7.21-7.20 (1H, m), 6.74 (1H, d, J=8.2 Hz), 6.31 (1H, s), 5.45 (2H, s), 3.54 (3H, s), 2.59 (3H, s), 2.26 (3H, s).

Intermediate compound 22A:
$^1$H-NMR (CDCl$_3$) δ: 7.45-7.41 (2H, m), 7.29-7.28 (1H, m), 7.24-7.23 (2H, m), 6.91 (1H, d, J=8.4 Hz), 5.08 (2H, s), 3.63 (3H, s), 2.52 (3H, s), 2.13 (3H, s), 2.08 (3H, s).

Intermediate compound 23A:
$^1$H-NMR (CDCl$_3$) δ: 7.52-7.41 (3H, m), 7.30-7.27 (2H, m), 6.88 (1H, d, J=8.4 Hz), 5.99 (1H, d, J=5.9 Hz), 5.08 (2H, s), 3.63 (3H, s), 2.51 (3H, s), 2.13 (3H, s).

Intermediate compound 24A:
$^1$H-NMR (CDCl$_3$) δ: 7.72 (1H, d, J=7.2 Hz), 7.57-7.49 (4H, m), 6.68 (1H, s), 6.13 (1H, s), 5.17 (2H, s), 3.69 (3H, s), 2.36 (3H, s), 2.35 (3H, s), 2.16 (3H, s).

The present compounds HA 101-1 to HA 109-120, HB 101-1 to HB 109-120, HC101-1 to HC 109-120, and HD 101-1 to HD 109-120 (hereinafter, referred to as Present compound A) may be obtained according to the similar method to the above-mentioned methods.

The present compound A represents any one of the compounds represented by the following formula (HA 101) to formula (HA 109), formula (HB 101) to formula (HB 109), formula (HC 101) to formula (HC 109), or formula (HD 101) to formula (HD 109) wherein $R^1$, $R^2$ and $R^3$ represent any one of the combinations selected from the group consisting of the following the substituent number 1 to 120.

For example, the present compound HA 104-5 represents a compound represented by formula (HA 104) wherein the substituent number is five(5), which represents a compound represented by the following structure.

[Chem.23]

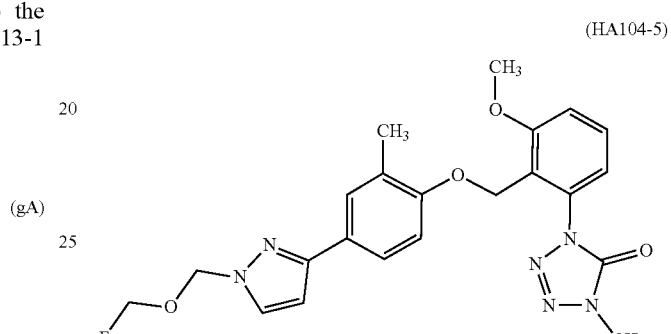

(HA104-5)

[Chem.24]

(HA101)

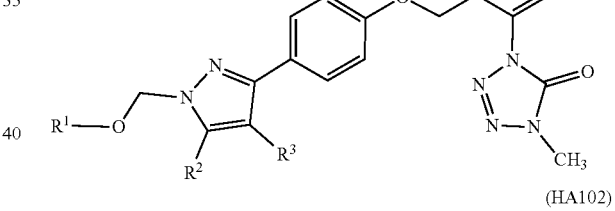

(HA102)

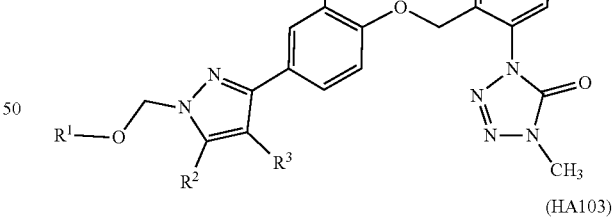

(HA103)

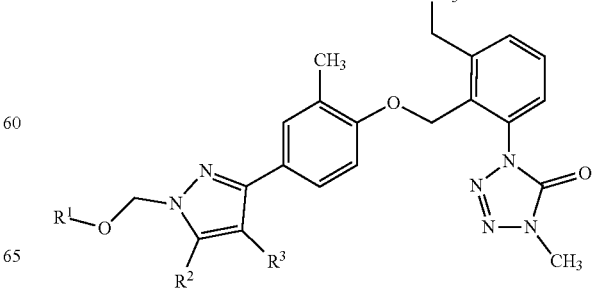

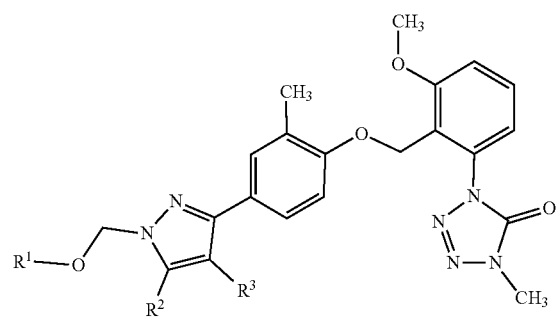
(HA104)
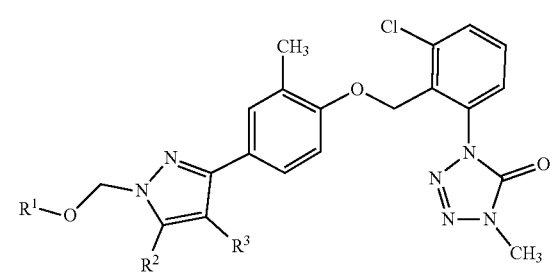
(HA105)
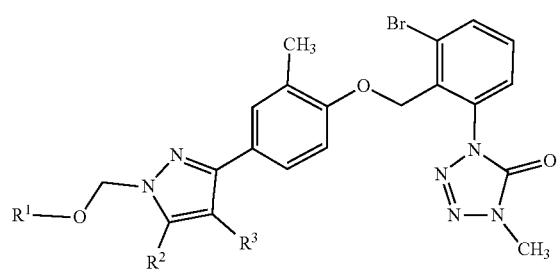
(HA106)
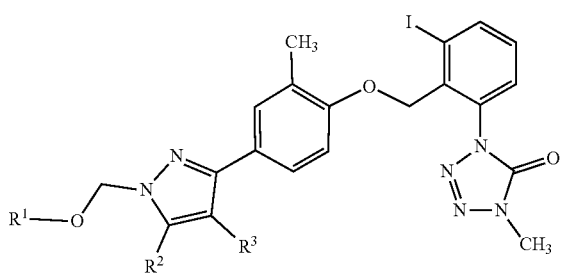
(HA107)
(HA108)
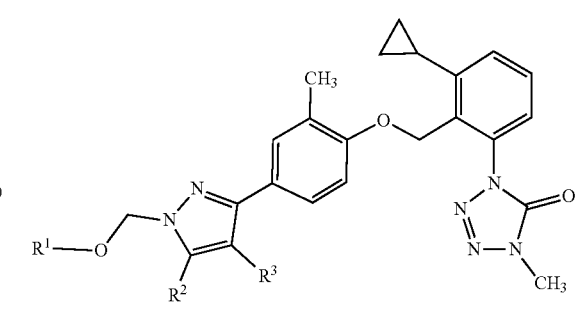
(HA109)
[Chem.25]
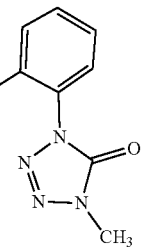
(HB101)
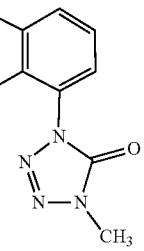
(HB102)
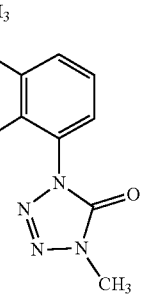
(HB103)
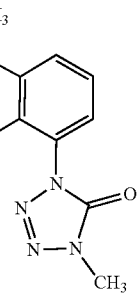
(HB104)

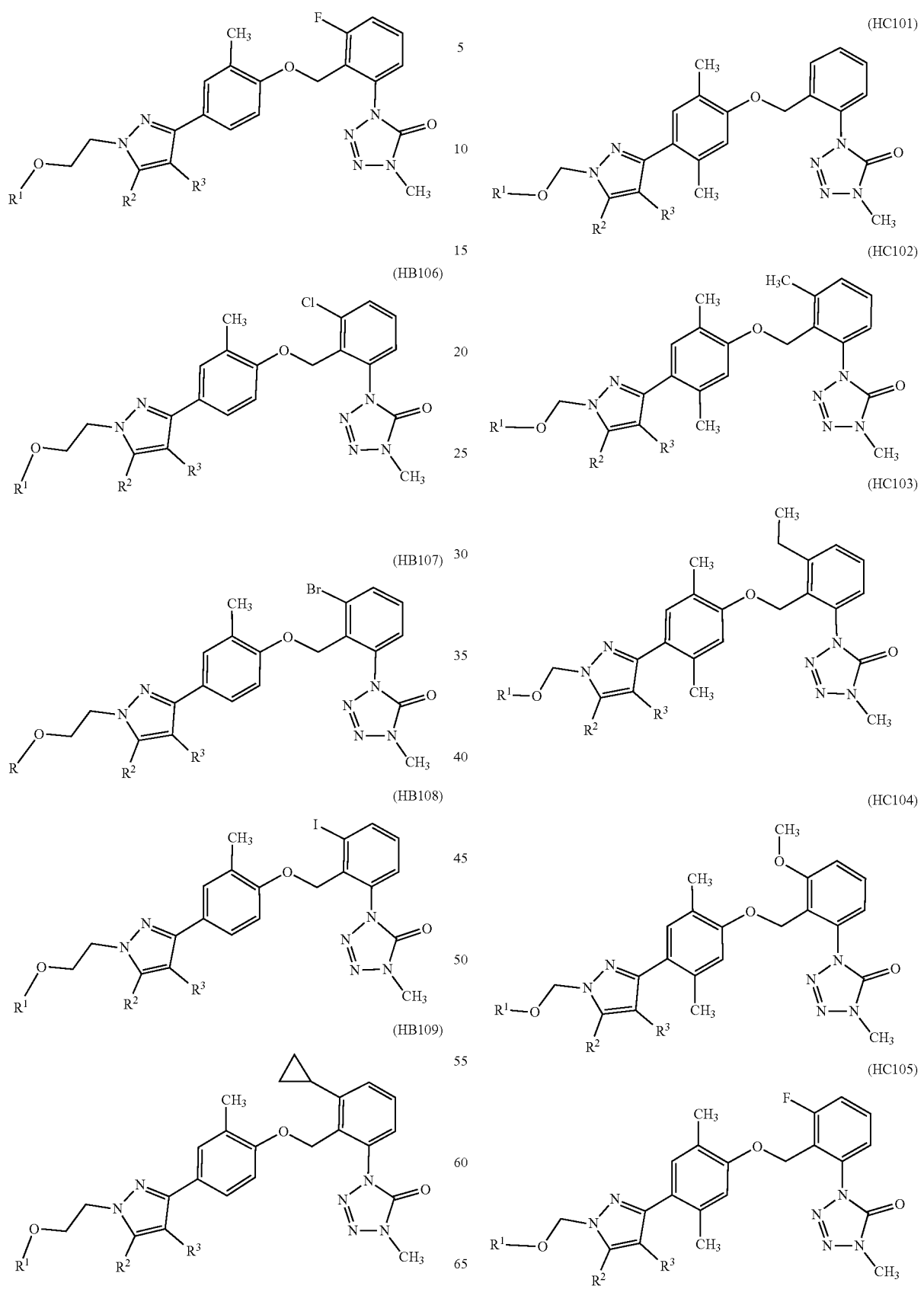

(HC106)
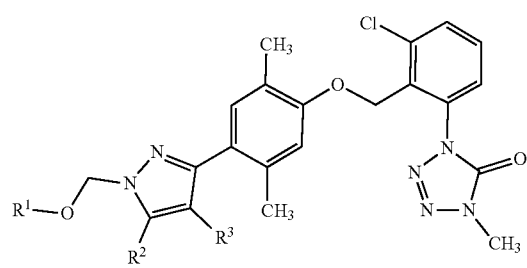
(HC107)
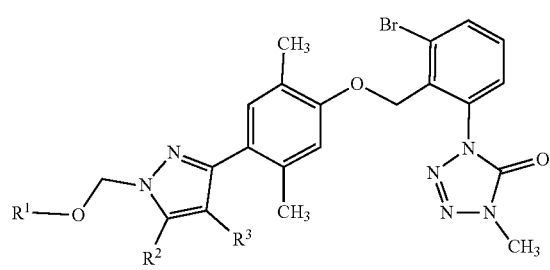
(HC108)
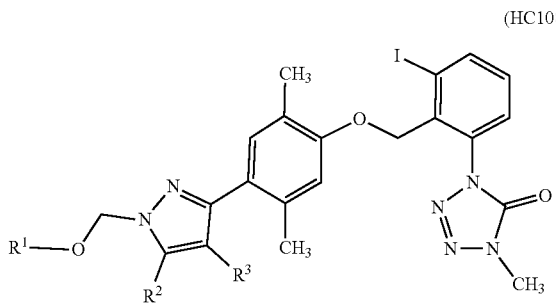
(HC109)
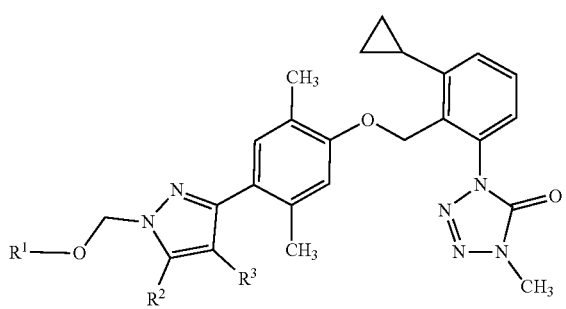
[Chem.27]
(HD101)
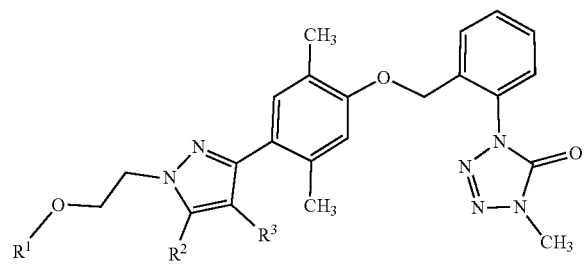
(HD102)
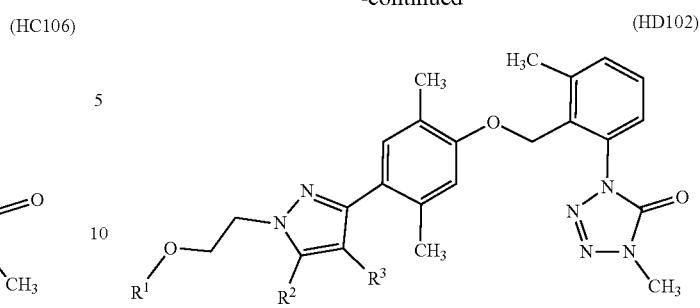
(HD103)
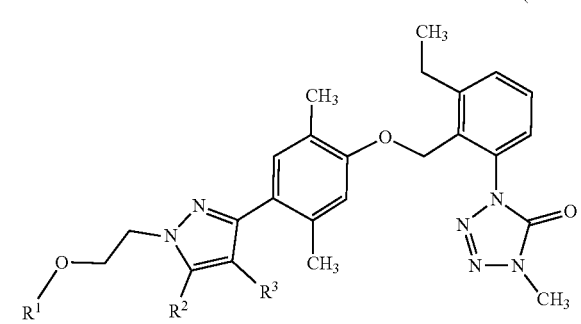
(HD104)
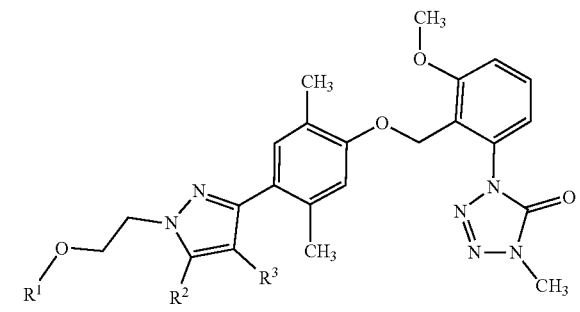
(HD105)
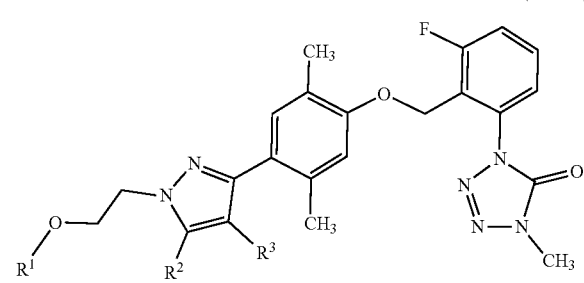
(HD106)
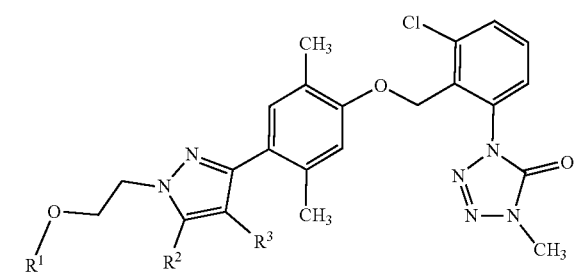

-continued

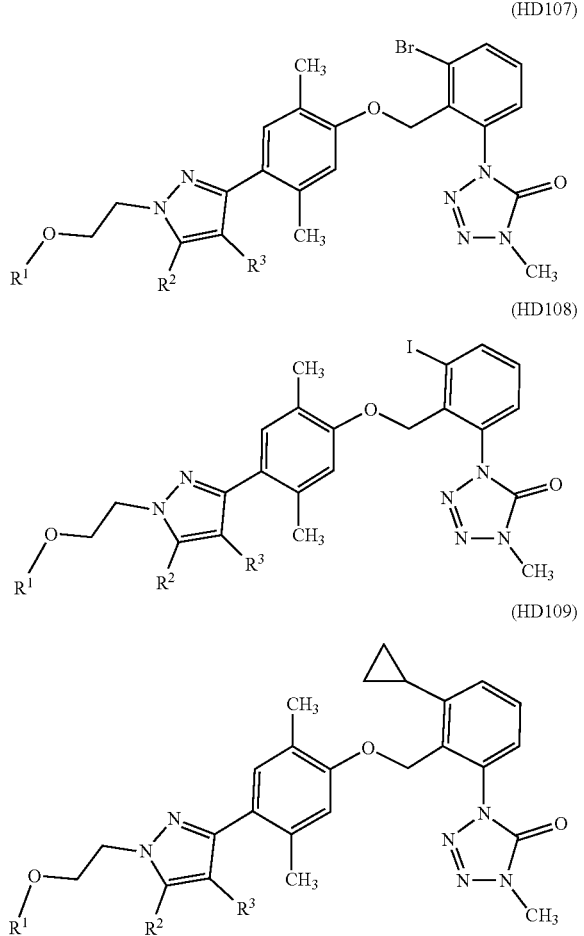

(SubstituentNumber; R¹, R², R³)

[1; CH₃,H,H], [2; CH₃CH₂,H,H], [3; (CH₃)₂CH,H,H], [4; CH₃CH₂CH₂,H,H], [5; CH₂F,H,H], [6; CHF₂,H,H], [7; CF₃,H,H], [8; CHF₂CH₂,H,H], [9; CF₃CH₂,H,H], [10; CHF₂CF₂,H,H], [11; CF₃CF₂,H,H], [12; CH₂Cl,H,H], [13; CHCl₂,H,H], [14; CCl₃,H,H], [15; CH₂ClCH₂,H,H], [16; CHCl₂CH₂,H,H], [17; CCl₃CH₂,H,H], [18; CHCl₂CCl₂,H,H], [19; CH₃,CH₃,H], [20; CH₃CH₂,CH₃,H], [21; (CH₃)₂CH,CH₃,H], [22; CH₃CH₂CH₂,CH₃,H], [23; CH₂F,CH₃,H], [24; CHF₂,CH₃,H], [25; CF₃,CH₃,H], [26; CHF₂CH₂,CH₃,H], [27; CF₃CH₂,CH₃,H], [28; CHF₂CF₂,CH₃,H], [29; CF₃CF₂,CH₃,H], [30; CH₂Cl,CH₃,H], [31; CHCl₂,CH₃,H], [32; CCl₃,CH₃,H], [33; CH₂ClCH₂,CH₃,H], [34; CHCl₂CH₂,CH₃,H],H[35; CCl₃CH₂,CH₃,H], [36; CHCl₂CCl₂,CH₃,H], [37; CH₃,H,CH₃], [38; CH₃CH₂,H,CH₃], [39; (CH₃)₂CH,H,CH₃], [40; CH₃CH₂CH₂,H,CH₃], [41; CH₂F,H,CH₃], [42; CHF₂,H,CH₃], [43; CF₃,H,CH₃], [44; CHF₂CH₂,H,CH₃], [45; CF₃CH₂,H,CH₃], [46; CHF₂CF₂,H,CH₃], [47; CF₃CF₂,H,CH₃], [48; CH₂Cl,H,CH₃], [49; CHCl₂,H,CH₃], [50; CCl₃,H,CH₃], [51; CH₂ClCH₂,H,CH₃], [52; CHCl₂CH₂,H,CH₃], [53; CCl₃CH₂,H,CH₃], [54; CHCl₂CCl₂,H,CH₃], [55; CH₃,CH₃,CH₃], [56; CH₃CH₂,CH₃,CH₃], [57; (CH₃)₂CH,CH₃,CH₃], [58; CH₃CH₂CH₂,CH₃,CH₃], [59; CH₂F,CH₃,CH₃], [60; CHF₂,CH₃,CH₃ ], [61; CF₃,CH₃,CH₃], [62; CHF₂CH₂,CH₃,CH₃], [63; CF₃CH₂,CH₃,CH₃], [64; CHF₂CF₂,CH₃,CH₃], [65; CF₃CF₂,CH₃,CH₃], [66; CH₂Cl,CH₃,CH₃], [67; CHCl₂,CH₃,CH₃], [68; CCl₃,CH₃,CH₃], [69; CH₂ClCH₂,CH₃,CH₃], [70; CHCl₂CH₂,CH₃,CH₃], [71; CHCl₂CCl₂,CH₃,CH₃], [72; CCl₃CCl₂,CH₃,CH₃], [73; CH₃,F,H], [74; CH₃CH₂,F,H], [75; (CH₃)₂CH,F,H], [76; CH₃CH₂CH₂,F,H], [77; CH₂F,Cl,H], [78; CHF₂,Cl,H], [79; CF₃,Cl,H], [80; CHF₂CH₂,Cl,H], [81; CF₃CH₂,Br,H], [82; CHF₂CF₂,Br,H], [83; CF₃CF₂,Br,H], [84; CH₂Cl,Br,H], [85; CHCl₂,F,CH₃], [86; CCl₃,F,CH₃], [87; CH₂ClCH₂,F,CH₃], [88; CHCl₂CH₂,F,CH₃], [89; CHCl₂CCl₂,Cl,CH₃], [90; CCl₃CCl₂,Cl,CH₃], [91; CH₃,Cl,CH₃ ], [92; CH₃CH₂,Cl,CH₃], [93; (CH₃)₂CH,Br,CH₃], [94; CH₃CH₂CH₂,Br,CH₃], [95; CH₂F,Br,CH₃], [96; CHF₂,Br,CH₃], [97; CF₃,H,F], [98; CHF₂CH₂,H,F], [99; CF₃CH₂,H,F], [100; CHF₂CF₂,H,F], [101; CF₃CF₂,H,Cl], [102; CH₂Cl,H,Cl], [103; CHCl₂,H,Cl], [104; CCl₃,H,Cl], [105; CH₂ClCH₂,H,Br], [106; CHCl₂CH₂,H,Br], [107; CHCl₂CCl₂,H,Br], [108; CCl₃CCl₂,H,Br], [109; CH₃,CH₃,F], [110; CH₃CH₂,CH₃,F], [111; (CH₃)₂CH,CH₃,F], [112; CH₃CH₂CH₂,CH₃,F], [113; CH₃,CH₃,Cl], [114; CH₃CH₂,CH₃,Cl], [115; (CH₃)₂CH,CH₃,Cl], [116; CH₃CH₂CH₂,CH₃,Cl], [117; CH₃,CH₃,Br], [118; CH₃CH₂,CH₃,Br], [119; (CH₃)₂CH,CH₃,Br], [120; CH₃CH₂CH₂,CH₃,Br].

The present compound may be mixed or combined with fungicides, insecticides, miticides, nematicides, plant growth regulators, or synergists (hereinafter, collectively referred to as Present active ingredient). Examples of the combination of the present compound with the present active ingredient are described below. For example, tebuconazole+SX represents a combination of tebuconazole with SX. The symbol of "SX" represents any one of the compound selected from the present compounds A. The numerical number in bracket represents a CAS register number.

tebuconazole+SX, prothioconazole+SX, metconazole+SX, ipconazole+SX, triti-conazole+SX, difenoconazole+SX, imazalil+SX, triadimenol+SX, tetraconazole+SX, flutriafol+SX, bromuconazole+SX, propiconazole+SX, mefentrifluconazole+SX, ipfentrifluconazole+SX, epoxiconazole+SX, cyproconazole+SX, mandestrobin+SX, azoxystrobin+SX, pyraclostrobin+SX, trifloxystrobin+SX, fluoxastrobin+SX, picoxystrobin+SX, fenamidone+SX, dimoxystrobin+SX, metominostrobin+SX, pyribencarb+SX, sedaxane+SX, penflufen+SX, fluxapyroxad+SX, fluopyram+SX, benzovindiflupyr+SX, boscalid+SX, carboxin+SX, penthiopyrad+SX, flutolanil+SX, bixafen+SX, pydiflumetofen+SX, 3-(difluoromethyl)-N-(7-fluoro-1,1,3-trimethylindan-4-yl)-1-methylpyrazole-4-carboxamide (1383809-87-7)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-(difluoromethyl)-1-methyl-N-(1,1,3-trimethylindan)-4-yl)pyrazole-4-carboxamide (141573-94-6)+SX, 3-(difluoromethyl)-1-methyl-N-[(3R)-1,1,3-trimethylindan-4-yl]pyrazole-4-carboxamide (1352994-67-2)+SX, metalaxyl+SX, metalaxyl-M+SX, metrafenone+SX, cyflufenamid+SX, proquinazid+SX, 3-chloro-5-phenyl-6-methyl-4-(2,6-difluorophenyl)pyridazine (1358061-55-8)+SX, 1-[2-({[1-(4-chlorophenyl)-1H-pyrazol-3-yl]oxy}methyl)-3-methylphenyl]-4-ethyl-4,5-dihydrotetrazole-5-one (1472649-01-6)+SX, 4-(2-bromo-4-fluorophenyl)-N-(2-chloro-6-fluorophenyl)-1,3-dimethyl-1H-pyrazole-5-amine (1362477-26-6)+SX, fenpicoxamid+SX, N'-(2,5-dimethyl-4-phenoxyphenyl)-N-ethyl-N-methyl methanimidamide (1052688-31-9)+SX, isotianil+SX, oxolinic acid+SX, ferimzone+SX, phthalide+SX, kasugamycin+SX, tebufloquin+SX, quinofumelin+SX, fenpyrazamin+SX, procymidone+SX, fludioxonil+SX, tolclofos-methyl+SX, thiabendazole+SX, ethaboxam+SX, picarbutrazox+SX, oxathiapiprolin+SX, iminoctadine triacetate+SX, iminoctadine albesilate+SX, fenpropimorph+SX, fenpropidin+SX, spiroxamine+SX, chlorothalonil+SX, folpet+SX, captan+SX, thiram+SX, silthiofam+SX, mancozeb+SX, cartap+SX, clothianidin+SX, thiamethoxam+SX, imidacloprid+SX, thiacloprid+SX, flupyradifurone+SX, sulfoxaflor+SX, tri-flumezopyrim+SX, dicloromezotiaz+SX, beta-cyfluthrin+SX, tefluthrin+SX, fipronil+SX, chlorantraniliprole+SX, cyantraniliprole+SX, tetraniliprole+SX, thiodicarb+SX, carbofuran+SX, fluxametamide+SX, afoxolaner+SX, fluralaner+SX, broflanilide+SX, abamectin+SX, fluensulfone+SX, fluazaindolizine+SX, tioxazafen+SX, a compound represente by the following formula:

[Chem.28]

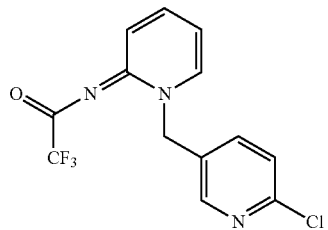

(1689566-03-7)+SX, Mycorrhiza Fungi+SX, *Bacillus firmus*+SX, *Bacillus amyloliquefaciens*+SX, *Pasteuria nishizawae*+SX, and *Pasteuria penetrans*+SX.

Though the mixed ratio of the present compound to the present ingredient is not particularly limited, examples of the weight ratio (the present compound:the present ingredient) is within a range of 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10.

An application of the present compound can provide an effect of a promotion of the growth of a plant, such as an increase in the rate of seedling establishment, an increase in the number of healthy leaves, an increase in the height of the plant, increase in the weight of the plant, an increase in the leaf area, increase in the number or weight of seeds or fruits, an increase in the number of occasion of flower setting or fruit setting, promoted growth of a root and the like. Also, an application of the present compound can provide an increase of a resistance against an abiotic stress such as a temperature stress (for example, high-temperature stress or low-temperature stress), water stress (for example, drought stress or excess water stress), and a salt stress.

Next, the Formulation Examples are described.

Formulation Example 1

Fifty (50) parts of any one of the present compounds A, 3 parts of calcium lignosulfonate, 2 parts of magnesium lauryl sulfate, and 45 parts of synthetic hydrated silicon dioxide are mixed-grinding to obtain a formulation.

Formulation Example 2

Twenty (20) parts of any one of the present compounds A, 1.5 parts of sorbitan trioleate are mixed with 28.5 parts of an aqueous solution containing 2 parts of polyvinyl alcohol, and the mixture is then finely-ground by a wet grinding method. To the mixture is then added 40 parts of an aqueous solution containing 0.05 parts of xanthan gum and 0.1 parts of magnesium aluminum silicate, and 10 parts of propylene glycol is further added thereto. The mixture is stirred to obtain a formulation.

Formulation Example 3

Two (2) parts of any one of the present compounds A, 88 parts of kaolin clay and 10 parts of talc are mixed-grinding to obtain a formulation.

Formulation Example 4

Five (5) parts of any one of the present compounds A, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the present compounds A, 1 part of synthetic hydrated silicon dioxide, 2 parts of calcium lignosulfonate, 30 parts of bentonite and 65 parts of kaolin clay are mixed-grinding and thereto is added water, and the mixture is well kneaded and is then granulated and dried to obtain a formulation.

Formulation Example 6

Thirty five (35) parts of a mixture of ammonium polyoxyethylene alkyl ether sulfate and white carbon (weight ratio: 1:1), 20 parts of any one of the present compounds A, and 45 parts of water are well mixed to obtain a formulation.

Next, Test Examples are used to show an efficacy of the present compounds on controlling plant diseases.

Test Example 1

A plastic pot was filled with soil and thereto barley (cv; Nishinohoshi) seeds were sown and the plants were grown in a greenhouse for 7 days. Thereafter, any of the present compounds 1, 2, 3, 4, 5, 7, 8, 11, 12, 16, 17, 19, 20, 21, 22, 23, 25, 26, 27 and 28 each of which was made to a formulation according to the similar method to that of Formulation Example 6, was adjusted with water so as to be 500 ppm. The adjusted solutions were sprayed to foliar parts so as to adhere adequately on the leaves of the above-mentioned barley. After spraying the adjusted solutions, the plants were air-dried and after 2 days, an aqueous suspension of the spores of barley net blotch fungi (*Pyrenophora teres*) was spraying-inoculated. After the inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present compounds 1, 2, 3, 4, 5, 7, 8, 11, 12, 16, 17, 19, 20, 21, 22, 23, 25, 26, 27 and 28 showed 10% or less compared to the lesion are in an untreated plants.

Test Example 2

A plastic pot was filled with soil and thereto rice (cv; Nipponbare) seeds were sown and the plants were grown in a greenhouse for twenty days. Thereafter, any of the present compounds 2, 3, 6, 7, 8, 10, 11, 12, 13, 14, 15, 16, 17, 27 and 28 each of which was made to a formulation according to the similar method to that of Formulation Example 6, was adjusted with water so as to be 500 ppm. The adjusted solutions were sprayed to foliar parts so as to adhere adequately on the leaves of the above-mentioned rice. After spraying the adjusted solutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present compounds 2, 3, 6, 7, 8, 10, 11, 12, 13, 14, 15, 16, 17, 27 and 28 showed 10% or less compared to the lesion are in an untreated plants.

Test Example 3

A plastic pot was filled with soil and thereto Kidney bean (cv; Nagauzurasaitou) seeds were sown and the plants were grown in a greenhouse for 8 days. Thereafter, any of the present compounds 1, 2, 3, 4, 5, 6, 7, 8, 10, 11, 12, 13, 14, 15, 16, 17, 19, 20, 21, 22, 25, 26, 27 and 28 each of which was made to a formulation according to the similar method to that of Formulation Example 6, was adjusted with water so as to be 500 ppm. The adjusted solutions were sprayed to foliar parts so as to adhere adequately on the leaves of the above-mentioned kidney bean. After spraying the adjusted solutions, the plants were air-dried and a PDA medium containing hyphae of kidney bean *sclerotinia* rot fungi (*Sclerotinia sclerotiorum*) was placed on the leaves of the kidney bean. After the inoculation, all kidney beans were placed under a high humidity during only night and after four days, a lesion area was observed. As a result, every of the lesion areas in plants treated with either the present compounds 1, 2, 3, 4, 5, 6, 7, 8, 10, 11, 12, 13, 14, 15, 16, 17, 19, 20, 21, 22, 25, 26, 27 and 28 showed 10% or less compared to the lesion area in an untreated plants.

Test Example 4

A plastic pot was filled with soil and thereto wheat (cv; Apogee) seeds were sown and the plants were grown in a greenhouse for 10 days. Thereafter, any of the present compounds 1, 2, 3, 4, 5, 6, 7, 8, 10, 11, 12, 13, 14, 15, 16, 17, 20, 21, 22, 26, 27 and 28 each of which was made to a formulation according to the similar method to that of Formulation Example 6, was adjusted with water so as to be 500 ppm. The adjusted solutions were sprayed to foliar parts so as to adhere adequately on the leaves of the above-mentioned wheat. After spraying the adjusted solutions, the plants were air-dried and after 4 days, an aqueous suspension of the spores of wheat leaf blotch fungi (*Septoria tritici*) was spraying-inoculated. After the inoculation, the plants were placed at 18° C. under a high humidity for 3 days and then under lighting for 14 to 18 days, and a lesion area was observed. As a result, every of the lesion areas in plants treated with the present compounds 1, 2, 3, 4, 5, 6, 7, 8, 10, 11, 12, 13, 14, 15, 16, 17, 20, 21, 22, 26, 27 and 28 showed 10% or less compared to the lesion area in an untreated plants.

Test Example 5

A plastic pot was filled with soils and thereto cucumber (cv; Sagamihanjiro) seeds were sown and the plants were grown in a greenhouse for 12 days. Thereafter, any of the present compounds 2, 3, 7, 8, 10, 11, 12, 13, 15, 16, 17, 20, 21, 22, 25, 26, 27 and 28 each of which was made to a formulation according to the similar method to that of Formulation Example 6, was adjusted with water so as to be 500 ppm. The adjusted solutions were sprayed to foliar parts so as to adhere adequately on the leaves of the above-mentioned cucumber. After spraying the adjusted solutions, the plants were air-dried and the spores of powdery mildew fungi (*Sphaerotheca fuliginea*; a QoI resistant strains where among the genes coding cytochrome b, a glycine residue as an amino acid residue at the 143rd of the cytochrome b is mutated to an alanine residue) were sprinkling-inoculated. The plants were placed in a greenhouse of 24° C. during daytime and 20° C. during nighttime for 8 days, and a lesion area was observed. As a result, every of the lesion areas in plants treated with the present compounds 2, 3, 7, 8, 10, 11, 12, 13, 15, 16, 17, 20, 21, 22, 25, 26, 27 and 28 showed 10% or less compared to the lesion area in an untreated plants.

Test Example 6

A plastic pot was filled with soil and thereto soybean (cv: Kurosengoku) seeds were sown and the plants were grown in a greenhouse for 13 days. Thereafter, any of the present compounds 1, 2, 3, 5, 6, 7, 8, 9, 10, 11, 12, 13, 14, 15, 16, 17, 18, 19, 20, 21, 23, 24, 25, 26, 27 and 28 each of which was made to a formulation according to the similar method to that of Formulation Example 6, was adjusted with water so as to be 200 ppm. The adjusted solutions were sprayed to foliar parts so as to adhere adequately on the leaves of the above-mentioned soybean. After spraying the adjusted solutions, the plants were air-dried and after 4 days, an aqueous suspension of the spores of soybean rust fungi (*Phakopsora pachyrhizi*) was spraying-inoculated. After the inoculation, the plants were placed in a greenhouse of 23° C. during daytime and 20° C. during nighttime under a high humidity for 3 days and were then cultivated in the greenhouse for 14 days, and a lesion area was observed. As a result, every of the lesion areas in plants treated with the present compounds 1, 2, 3, 5, 6, 7, 8, 9, 10, 11, 12, 13, 14, 15, 16, 17, 18, 19, 20, 21, 23, 24, 25, 26, 27 and 28 showed 10% or less compared to the lesion area in an untreated plants.

Test Example 7

A plastic pot was filled with soil and thereto barley (cv; Nishinohoshi) seeds were sown and the plants were grown in a greenhouse for 7 days. Thereafter, any of the present compounds 1, 2, 3, 4, 5, 6, 7, 8, 9, 10, 11, 12, 13, 14, 15, 16, 17, 18, 19, 20, 21, 22, 23, 25, 26, 27 and 28 each of which was made to a formulation according to the similar method to that of Formulation Example 6, was adjusted with water so as to be 200 ppm. The adjusted solutions were sprayed to foliar parts so as to adhere adequately on the leaves of the above-mentioned barley. After spraying the adjusted solutions, the plants were air-dried and after 1 days, an aqueous suspension of the spores of barley leaf blotch fungi (*Rhynchosporium secalis*) was spraying-inoculated. After the inoculation, the plants were placed at 15° C. under a high humidity for 3 days, and were then cultivated in the greenhouse for 14 days, and a lesion area was observed. As a result, every of the lesion areas in plants treated with the present compounds 1, 2, 3, 4, 5, 6, 7, 8, 9, 10, 11, 12, 13, 14, 15, 16, 17, 18, 19, 20, 21, 22, 23, 25, 26, 27 and 28 showed 10% or less compared to the lesion area in an untreated plants.

Test Example 8

A plastic pot was filled with soil and thereto cucumber (cv; Sagamihanjiro) seeds were sown and the plants were grown in a greenhouse for 19 days. Thereafter, any of the present compounds 6, 9, 10, 13, 14 and 15 each of which was made to a formulation according to the similar method to that of Formulation Example 6, was adjusted with water so as to be 200 ppm. The adjusted solutions were sprayed to foliar parts so as to adhere adequately on the leaves of the above-mentioned cucumber. After spraying the adjusted solutions, the plants were air-dried and after 1 day, an aqueous suspension of the spores of cucumber anthracnose fungi (*Colletotrichum lagenarium*) was spraying-inoculated. After the inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present compounds 6, 9, 10, 13, 14 and 15 showed 10% or less compared to the lesion area in an untreated plants.

Test Example 9

A plastic pot was filled with soil and thereto cucumber (cv; Sagamihanjiro) seeds were sown and the plants were grown in a greenhouse for 19 days. Thereafter, any of the present compounds 1, 4, 5, 6, 10, 13, 14, 16 and 17 each of which was made to a formulation according to the similar method to that of Formulation Example 6, was adjusted with water so as to be 50 ppm. The adjusted solutions were sprayed to foliar parts so as to adhere adequately on the leaves of the above-mentioned cucumber. After spraying the adjusted solutions, the plants were air-dried and after 1 day, an aqueous suspension of the zoospores of cucumber downy mildew fungi (*Pseudoperonospora cubensis*) was spraying-inoculated. After the inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present compounds 1, 4, 5, 6, 10, 13, 14, 16 and 17 showed 10% or less compared to the lesion area in an untreated plants.

Test Example 10

A plastic pot was filled with soil and thereto soybean (cv.; Tachinagaha) seeds were sown and the plants were grown in a greenhouse for 13 days. Thereafter, an aqueous suspension of the spores of soybean frogeye leaf spot (*Cercospora sojina*) was spraying-inoculated. After the inoculation, the plants were placed in a greenhouse of 23° C. under a high humidity for 4 days. After 5 days, any of the present compounds 1, 3, 4, 5, 7 and 20 each of which was made to a formulation according to the similar method to that of Formulation Example 6, was adjusted with water so as to be 200 ppm. The adjusted solutions were sprayed to foliar parts so as to adhere adequately on the leaves of the above-mentioned soybean. After spraying the adjusted solutions, the plants were air-dried and were then cultivated in a greenhouse for 14 days, and a lesion area was observed. As a result, every of the lesion areas in plants treated with the present compounds 1, 3, 4, 5, 7 and 20 showed 10% or less compared to the lesion area in an untreated plants.

Test Example 11

A plastic pot was filled with soil and thereto cucumber (cv; Sagamihanjiro) seeds were sown and the plants were grown in a greenhouse for 14 days. Thereafter, any of the present compounds 1, 3, 6, 9, 10, 14 and 16 each of which was made to a formulation according to the similar method to that of Formulation Example 6, was adjusted with water so as to contain 0.25 mg/L, and the roots of the cucumber seedlings were immersed into the adjusted solutions. After 8 days, a PDA medium containing hyphae of cucumber *sclerotinia* rot fungi (*Sclerotinia sclerotiorum*) was placed on the leaves of the cucumber. After the inoculation, all the cucumbers were placed only during nighttime under a high humidity, and after 4 days, a lesion area was observed. As a result, every of the lesion areas in plants treated with the present compounds 1, 3, 6, 9, 10, 14 and 16 showed 10% or less compared to the lesion area in an untreated plants.

Test Example 12

Any of the present compounds 2, 3, 4, 5, 6, 7, 8, 9, 10, 11, 12, 13, 14, 15, 18, 19, 20, 21, 22, 23, 24, 25, 26, 27 and 28 was diluted with dimethyl sulfoxide so as to contain 150 ppm, and 1 L portion of the dilute solution was dispensed into a titer plate (96 wells), and thereto was then dispensed 150 μL of a potato dextrose broth medium (PDB medium) containing spores of leaf mold (*Cladosporium fulvum*; a QoI resistant strains where among the genes coding cytochrome b, a phenylalanine residue as an amino acid residue at the 129th of the cytochrome b is mutated to an Leucine residue). This plate was cultured at 18° C. for 6 days, thereby allowing the tomato leaf mold fungi to undergo proliferation, and the absorbance at 550 nm of each well of the tilter plate was then measured to determine a degree of growth of tomato leaf mold fungi. The inhibitory ratio was calculated from the determined degree of growth by the below-mentioned Equation.

$$\text{Inhibitory ratio}=100\times(A-B)/A \qquad \text{"Equation"}$$

where
A: Degree of fungal growth in non-treated area
B: Degree of fungal growth in treated area
As a result, the inhibitory ratio of each well treated with every of the present compounds 2, 3, 4, 5, 6, 7, 8, 9, 10, 11, 12, 13, 14, 15, 18, 19, 20, 21, 22, 23, 24, 25, 26, 27 and 28 was 80% or more.

Test Example 13

A plastic pot was filled with soil and thereto wheat (cv; Shirogane) seeds were sown and the plants were grown in a greenhouse for 9 days. Any of the present compounds 1, 2, 3, 5, 6, 7, 8, 9, 10, 12, 13, 14, 15, 18, 19, 20, 21, 26, 27 and 28 each of which was made to a formulation according to the similar method to that of Formulation Example 6, was adjusted with water so as to be 12.5 ppm, and the adjusted solutions were sprayed to foliar parts so as to adhere adequately on the leaves of the above-mentioned wheat. After spraying the adjusted solutions, the plants were air-dried and were then cultivated at 20° C. under lighting for 5 days. The spores of wheat rust fungi (*Puccinia recondita*) were sprinkling-inoculated. After the inoculation, the plants were placed under a dark and humid condition at 23° C. for 1 day and were then cultivated at 20° C. under lighting for 8 days, and a lesion area was observed. As a result, every of the lesion areas in plants treated with the present compounds 1, 2, 3, 5, 6, 7, 8, 9, 10, 12, 13, 14, 15, 18, 19, 20, 21, 26, 27 and 28 showed 30% or less compared to the lesion area in an untreated plants.

Comparative Test Example 1

A plastic pot was filled with soils and thereto was seeded wheat (cv; Shirogane) and the plants were grown in a greenhouse for 9 days. 1-(2-{[2-methyl-4-(1-methyl-1H-pyrazol-3-yl)phenoxy]methyl}-3-methylphenyl)-4-m ethyl-4,5-dihydrotetrazole-5-one which was made to a formulation according to the similar method to that of Formulation Example 6 was adjusted with water so as to be 12.5 ppm. The adjusted solutions were sprayed to foliar parts so as to adhere adequately on the leaves of the above-mentioned wheat. After spraying the adjusted solutions, the plants were air-dried and were then cultivated at 20° C. under lighting for 5 days. The spores of wheat rust fungi (*Puccinia recondita*) were sprinkling-inoculated. After the inoculation, the plants were placed under a dark and humid condition at 23° C. for 1 day and were then cultivated at 20° C. under lighting for 8 days, and a lesion area was observed. As a result, the lesion area in plants treated with 1-(2-{[2-methyl-4-(1-methyl-1H-pyrazol-3-yl)phenoxy]methyl}-3-methylphenyl)-4-m ethyl-4,5-dihydrotetrazole-5-one showed 70% or more compared to the lesion area in an untreated plants.

INDUSTRIAL APPLICABILITY

The compound of the present invention has efficacies for controlling plant diseases, and is useful as an active ingredient for an agent for controlling plant diseases.

The invention claimed is:

1. A compound represented by a formula (I):

[Chem. 1]

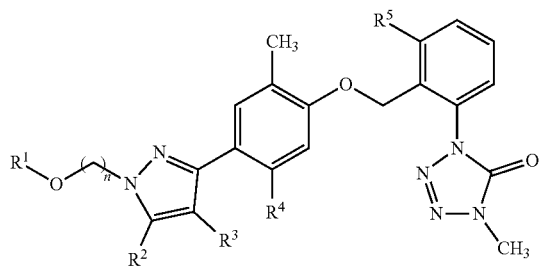

(I)

wherein, $R^1$ represents a C1-C3 alkyl group optionally having one or more halogens;

n is 1 or 2;

$R^2$ and $R^3$ each independently represent a hydrogen atom, a halogen atom, or a C1-C3 alkyl group;

$R^4$ represents a hydrogen atom or a methyl group; and $R^5$ represents a C1-C3 alkyl group optionally having one or more halogen atoms, a C1-C3 alkoxy group optionally having one or more halogen atoms, a hydrogen atom, a halogen atom, or a C3-C4 cycloalkyl group optionally having one or more halogen atoms.

2. The compound according to claim 1 wherein $R^1$ represents a C1-C3 alkyl group, $R^2$ and $R^3$ each independently represent a hydrogen atom, a halogen atom, or a methyl group; and $R^5$ represents a hydrogen atom, a halogen atom, a C1-C3 alkyl group, a C1-C3 alkoxy group or a cyclopropyl group.

3. The compound according to claim 1 wherein $R^2$ represents a hydrogen atom or a methyl group $R^3$ represents a hydrogen atom; and $R^5$ represents a C1-C3 alkyl group.

4. An agent for controlling a plant disease which comprises the compound as defined in claim 1.

5. A method for controlling plant diseases which comprises applying an effective amount of the compound as defined in claim 1 to plant or soil.

* * * * *